(12) United States Patent
Garrison

(10) Patent No.: US 9,931,158 B2
(45) Date of Patent: Apr. 3, 2018

(54) DEPLOYMENT MECHANISMS FOR SURGICAL INSTRUMENTS

(71) Applicant: COVIDIEN LP, Mansfield, MA (US)

(72) Inventor: David M. Garrison, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 445 days.

(21) Appl. No.: 14/802,423

(22) Filed: Jul. 17, 2015

(65) Prior Publication Data

US 2016/0074100 A1    Mar. 17, 2016

Related U.S. Application Data

(60) Provisional application No. 62/051,394, filed on Sep. 17, 2014, provisional application No. 62/051,389, (Continued)

(51) Int. Cl.
*A61B 18/14* (2006.01)
*A61B 17/29* (2006.01)
(Continued)

(52) U.S. Cl.
CPC .......... *A61B 18/1445* (2013.01); *A61B 17/29* (2013.01); *A61B 18/1447* (2013.01); (Continued)

(58) Field of Classification Search
CPC ............ A61B 18/1447; A61B 18/1445; A61B 18/1482; A61B 2017/2923;
(Continued)

(56) References Cited

U.S. PATENT DOCUMENTS

| 4,005,714 A | 2/1977 | Hiltebrandt |
|---|---|---|
| D249,549 S | 9/1978 | Pike |

(Continued)

FOREIGN PATENT DOCUMENTS

| AU | 2011253698 A1 | 12/2011 |
|---|---|---|
| CN | 21299462 | 9/2009 |

(Continued)

OTHER PUBLICATIONS

U.S. Appl. No. 08/926,869, James G. Chandler.
(Continued)

*Primary Examiner* — Jaymi Della

(57) ABSTRACT

A surgical instrument includes a housing, an energizable member selectively deployable relative to the housing, and a deployment mechanism. The deployment mechanism includes a fixed gear rotatable in opposite directions to move the energizable member between the deployed and storage positions. The deployment mechanism further includes an actuator assembly having a first actuator and a first gear, and a reversing assembly. The actuator assembly is movable relative to the fixed gear between an engaged position and a spaced-apart position. The reversing assembly includes a second actuator and a second gear that is movable between a removed position, wherein the first gear is disposed in the engaged position and the second gear is disengaged from the first gear and the fixed gear, and an inserted position, wherein the first gear is moved to the spaced-apart position and the second gear is engaged between the first gear and the fixed gear.

12 Claims, 10 Drawing Sheets

Related U.S. Application Data filed on Sep. 17, 2014, provisional application No. 62/051,391, filed on Sep. 17, 2014.

(51) Int. Cl.
- A61B 18/00 (2006.01)
- A61B 18/12 (2006.01)
- A61B 17/295 (2006.01)

(52) U.S. Cl.
CPC ..... *A61B 17/295* (2013.01); *A61B 2017/2902* (2013.01); *A61B 2017/2943* (2013.01); *A61B 2018/0063* (2013.01); *A61B 2018/00083* (2013.01); *A61B 2018/00184* (2013.01); *A61B 2018/00601* (2013.01); *A61B 2018/126* (2013.01); *A61B 2018/1253* (2013.01)

(58) Field of Classification Search
CPC  A61B 2018/00196; A61B 2018/00577; A61B 2018/00589; A61B 2018/00595; A61B 2018/0063; A61B 2018/00922; A61B 2018/00952; A61B 2018/00958; A61B 2018/1253; A61B 2018/126; A61B 2018/1475; A61B 2018/00184; A61B 2018/00083; A61B 17/295
See application file for complete search history.

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,026,379 A | 6/1991 | Yoon |
| D343,453 S | 1/1994 | Noda |
| 5,312,391 A | 5/1994 | Wilk |
| 5,318,589 A | 6/1994 | Lichtman |
| 5,324,254 A | 6/1994 | Phillips |
| D348,930 S | 7/1994 | Olson |
| D349,341 S | 8/1994 | Lichtman et al. |
| 5,342,359 A | 8/1994 | Rydell |
| 5,368,600 A | 11/1994 | Failla et al. |
| D354,564 S | 1/1995 | Medema |
| 5,401,274 A | 3/1995 | Kusunoki |
| D358,887 S | 5/1995 | Feinberg |
| 5,411,519 A | 5/1995 | Tovey et al. |
| 5,445,638 A | 8/1995 | Rydell et al. |
| 5,458,598 A | 10/1995 | Feinberg et al. |
| 5,527,313 A | 6/1996 | Scott et al. |
| 5,556,397 A | 9/1996 | Long et al. |
| 5,611,813 A | 3/1997 | Lichtman |
| D384,413 S | 9/1997 | Zlock et al. |
| H1745 H | 4/1998 | Paraschac |
| 5,735,873 A | 4/1998 | MacLean |
| 5,792,164 A | 8/1998 | Lakatos et al. |
| 5,807,393 A | 9/1998 | Williamson, IV et al. |
| D402,028 S | 12/1998 | Grimm et al. |
| D408,018 S | 4/1999 | McNaughton |
| 5,893,863 A | 4/1999 | Yoon |
| 5,919,202 A | 7/1999 | Yoon |
| D416,089 S | 11/1999 | Barton et al. |
| 6,004,319 A | 12/1999 | Goble et al. |
| D424,694 S | 5/2000 | Tetzlaff et al. |
| D425,201 S | 5/2000 | Tetzlaff et al. |
| 6,113,596 A | 9/2000 | Hooven et al. |
| H1904 H | 10/2000 | Yates et al. |
| 6,156,009 A | 12/2000 | Grabek |
| 6,190,386 B1 | 2/2001 | Rydell |
| 6,270,497 B1 | 8/2001 | Sekino et al. |
| D449,886 S | 10/2001 | Tetzlaff et al. |
| 6,299,625 B1 | 10/2001 | Bacher |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| 6,387,094 B1 | 5/2002 | Eitenmuller |
| H2037 H | 7/2002 | Yates et al. |
| D465,281 S | 11/2002 | Lang |
| D466,209 S | 11/2002 | Bon |
| 6,551,313 B1 | 4/2003 | Levin |
| 6,558,385 B1 | 5/2003 | McClurken et al. |
| 6,679,882 B1 | 1/2004 | Kornerup |
| D493,888 S | 8/2004 | Reschke |
| D496,997 S | 10/2004 | Dycus et al. |
| 6,808,525 B2 | 10/2004 | Latterell et al. |
| D499,181 S | 11/2004 | Dycus et al. |
| 6,837,888 B2 | 1/2005 | Ciarrocca et al. |
| D502,994 S | 3/2005 | Blake, III |
| D509,297 S | 9/2005 | Wells |
| 6,942,662 B2 | 9/2005 | Goble et al. |
| 7,033,356 B2 | 4/2006 | Latterell et al. |
| 7,063,699 B2 | 6/2006 | Hess et al. |
| D525,361 S | 7/2006 | Hushka |
| D531,311 S | 10/2006 | Guerra et al. |
| 7,128,254 B2 | 10/2006 | Shelton, IV et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| 7,208,005 B2 | 4/2007 | Frecker et al. |
| D541,611 S | 5/2007 | Aglassinger |
| D541,938 S | 5/2007 | Kerr et al. |
| D545,432 S | 6/2007 | Watanabe |
| 7,232,440 B2 | 6/2007 | Dumbauld et al. |
| D547,154 S | 7/2007 | Lee |
| D564,662 S | 3/2008 | Moses et al. |
| D567,943 S | 4/2008 | Moses et al. |
| 7,367,976 B2 | 5/2008 | Lawes et al. |
| 7,402,162 B2 | 7/2008 | Ouchi |
| D575,395 S | 8/2008 | Hushka |
| D575,401 S | 8/2008 | Hixson et al. |
| 7,442,194 B2 | 10/2008 | Dumbauld et al. |
| 7,445,621 B2 | 11/2008 | Dumbauld et al. |
| D582,038 S | 12/2008 | Swoyer et al. |
| 7,481,810 B2 | 1/2009 | Dumbauld et al. |
| 7,510,562 B2 | 3/2009 | Lindsay |
| 7,588,570 B2 | 9/2009 | Wakikaido et al. |
| 7,658,311 B2 | 2/2010 | Boudreaux |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,758,577 B2 | 7/2010 | Nobis et al. |
| D621,503 S | 8/2010 | Otten et al. |
| 7,789,878 B2 | 9/2010 | Dumbauld et al. |
| 7,815,636 B2 | 10/2010 | Ortiz |
| 7,819,872 B2 | 10/2010 | Johnson et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,879,035 B2 | 2/2011 | Garrison et al. |
| D649,249 S | 11/2011 | Guerra |
| D649,643 S | 11/2011 | Allen, IV et al. |
| D661,394 S | 6/2012 | Romero et al. |
| 8,257,352 B2 | 9/2012 | Lawes et al. |
| 8,333,765 B2 | 12/2012 | Johnson et al. |
| 8,353,437 B2 | 1/2013 | Boudreaux |
| 8,454,602 B2 | 6/2013 | Kerr et al. |
| 8,523,898 B2 | 9/2013 | Bucciaglia et al. |
| 8,529,566 B2 | 9/2013 | Kappus et al. |
| 8,568,408 B2 | 10/2013 | Townsend et al. |
| 8,591,510 B2 | 11/2013 | Allen, IV et al. |
| 8,628,557 B2 | 1/2014 | Collings et al. |
| 8,679,098 B2 | 3/2014 | Hart |
| 8,679,140 B2 | 3/2014 | Butcher |
| RE44,834 E | 4/2014 | Dumbauld et al. |
| 8,685,009 B2 | 4/2014 | Chernov et al. |
| 8,685,056 B2 | 4/2014 | Evans et al. |

(56) References Cited

U.S. PATENT DOCUMENTS

| | | |
|---|---|---|
| 8,696,667 B2 | 4/2014 | Guerra et al. |
| 8,702,737 B2 | 4/2014 | Chojin et al. |
| 8,702,749 B2 | 4/2014 | Twomey |
| 8,745,840 B2 | 6/2014 | Hempstead et al. |
| 8,747,413 B2 | 6/2014 | Dycus |
| 8,747,434 B2 | 6/2014 | Larson et al. |
| 8,752,264 B2 | 6/2014 | Ackley et al. |
| 8,756,785 B2 | 6/2014 | Allen, IV et al. |
| 8,845,636 B2 | 9/2014 | Allen, IV et al. |
| 8,852,185 B2 | 10/2014 | Twomey |
| 8,864,753 B2 | 10/2014 | Nau, Jr. et al. |
| 8,864,795 B2 | 10/2014 | Kerr et al. |
| 8,887,373 B2 | 11/2014 | Brandt et al. |
| 8,888,771 B2 | 11/2014 | Twomey |
| 8,900,232 B2 | 12/2014 | Ourada |
| 8,920,461 B2 | 12/2014 | Unger et al. |
| 8,939,972 B2 | 1/2015 | Twomey |
| 8,961,513 B2 | 2/2015 | Allen, IV et al. |
| 8,961,514 B2 | 2/2015 | Garrison |
| 8,961,515 B2 | 2/2015 | Twomey et al. |
| 8,968,283 B2 | 3/2015 | Kharin |
| 8,968,298 B2 | 3/2015 | Twomey |
| 8,968,305 B2 | 3/2015 | Dumbauld et al. |
| 8,968,306 B2 | 3/2015 | Unger |
| 8,968,307 B2 | 3/2015 | Evans et al. |
| 8,968,308 B2 | 3/2015 | Horner et al. |
| 8,968,309 B2 | 3/2015 | Roy et al. |
| 8,968,310 B2 | 3/2015 | Twomey et al. |
| 8,968,311 B2 | 3/2015 | Allen, IV et al. |
| 8,968,317 B2 | 3/2015 | Evans et al. |
| 8,968,360 B2 | 3/2015 | Garrison et al. |
| 9,011,435 B2 | 4/2015 | Brandt et al. |
| 9,023,035 B2 | 5/2015 | Allen, IV et al. |
| 9,028,492 B2 | 5/2015 | Kerr et al. |
| 9,033,981 B2 | 5/2015 | Olson et al. |
| 9,034,009 B2 | 5/2015 | Twomey et al. |
| 9,039,691 B2 | 5/2015 | Moua et al. |
| 9,039,704 B2 | 5/2015 | Joseph |
| 9,039,732 B2 | 5/2015 | Sims et al. |
| 9,060,780 B2 | 6/2015 | Twomey et al. |
| 9,072,524 B2 | 7/2015 | Heard et al. |
| 9,113,882 B2 | 8/2015 | Twomey et al. |
| 9,113,899 B2 | 8/2015 | Garrison et al. |
| 9,113,901 B2 | 8/2015 | Allen, IV et al. |
| 9,113,909 B2 | 8/2015 | Twomey et al. |
| 9,113,933 B2 | 8/2015 | Chernova et al. |
| 9,113,934 B2 | 8/2015 | Chernov, et al. |
| 9,113,938 B2 | 8/2015 | Kerr |
| 9,161,807 B2 | 10/2015 | Garrison |
| 2002/0049442 A1 | 4/2002 | Roberts et al. |
| 2004/0236326 A1 | 11/2004 | Schulze et al. |
| 2005/0113827 A1 | 5/2005 | Dumbauld et al. |
| 2005/0187547 A1 | 8/2005 | Sugi |
| 2006/0015067 A1* | 1/2006 | Bates ............... A61B 17/3478 604/151 |
| 2006/0129146 A1 | 6/2006 | Dycus et al. |
| 2007/0078458 A1 | 4/2007 | Dumbauld et al. |
| 2007/0106295 A1 | 5/2007 | Garrison et al. |
| 2007/0213707 A1 | 9/2007 | Dumbauld et al. |
| 2007/0278277 A1 | 12/2007 | Wixey et al. |
| 2008/0083813 A1 | 4/2008 | Zemlok et al. |
| 2008/0215050 A1 | 9/2008 | Bakos |
| 2008/0243120 A1 | 10/2008 | Lawes et al. |
| 2009/0012556 A1* | 1/2009 | Boudreaux .......... A61B 17/068 606/206 |
| 2009/0112206 A1 | 4/2009 | Dumbauld et al. |
| 2009/0125026 A1 | 5/2009 | Rioux et al. |
| 2009/0125027 A1 | 5/2009 | Fischer |
| 2009/0131974 A1 | 5/2009 | Pedersen et al. |
| 2009/0171350 A1 | 7/2009 | Dycus et al. |
| 2009/0182327 A1 | 7/2009 | Unger |
| 2009/0254084 A1 | 10/2009 | Naito |
| 2010/0185196 A1 | 7/2010 | Sakao et al. |
| 2010/0185197 A1 | 7/2010 | Sakao et al. |
| 2010/0292690 A1 | 11/2010 | Livneh |
| 2011/0071525 A1 | 3/2011 | Dumbauld et al. |
| 2011/0087218 A1 | 4/2011 | Boudreaux et al. |
| 2011/0130757 A1 | 6/2011 | Horlle et al. |
| 2011/0264093 A1 | 10/2011 | Schall |
| 2011/0276049 A1* | 11/2011 | Gerhardt ............ A61B 18/1402 606/45 |
| 2011/0319886 A1 | 12/2011 | Chojin et al. |
| 2012/0083827 A1 | 4/2012 | Artale et al. |
| 2012/0209263 A1 | 8/2012 | Sharp et al. |
| 2012/0239034 A1 | 9/2012 | Horner et al. |
| 2012/0259331 A1 | 10/2012 | Garrison |
| 2012/0265241 A1 | 10/2012 | Hart et al. |
| 2012/0296205 A1 | 11/2012 | Chernov et al. |
| 2012/0296238 A1 | 11/2012 | Chernov et al. |
| 2012/0296239 A1 | 11/2012 | Chernov et al. |
| 2012/0296323 A1 | 11/2012 | Chernov et al. |
| 2012/0296371 A1 | 11/2012 | Kappus et al. |
| 2012/0303026 A1 | 11/2012 | Dycus et al. |
| 2012/0323238 A1 | 12/2012 | Tyrrell et al. |
| 2012/0330308 A1 | 12/2012 | Joseph |
| 2012/0330351 A1 | 12/2012 | Friedman et al. |
| 2013/0018364 A1 | 1/2013 | Chernov et al. |
| 2013/0022495 A1 | 1/2013 | Allen, IV et al. |
| 2013/0071282 A1 | 3/2013 | Fry |
| 2013/0072927 A1 | 3/2013 | Allen, IV et al. |
| 2013/0079760 A1 | 3/2013 | Twomey et al. |
| 2013/0079774 A1 | 3/2013 | Whitney et al. |
| 2013/0085496 A1 | 4/2013 | Unger et al. |
| 2013/0103030 A1 | 4/2013 | Garrison |
| 2013/0103031 A1 | 4/2013 | Garrison |
| 2013/0138101 A1 | 5/2013 | Kerr |
| 2013/0144284 A1 | 6/2013 | Behnke, II et al. |
| 2013/0165907 A1 | 6/2013 | Attar et al. |
| 2013/0197503 A1 | 8/2013 | Orszulak |
| 2013/0218198 A1 | 8/2013 | Larson et al. |
| 2013/0245623 A1 | 9/2013 | Twomey |
| 2013/0247343 A1 | 9/2013 | Horner et al. |
| 2013/0253489 A1 | 9/2013 | Nau, Jr. et al. |
| 2013/0255063 A1 | 10/2013 | Hart et al. |
| 2013/0267948 A1 | 10/2013 | Kerr et al. |
| 2013/0267949 A1 | 10/2013 | Kerr |
| 2013/0274736 A1 | 10/2013 | Garrison |
| 2013/0282010 A1 | 10/2013 | McKenna et al. |
| 2013/0289561 A1 | 10/2013 | Waaler et al. |
| 2013/0296854 A1 | 11/2013 | Mueller |
| 2013/0296922 A1 | 11/2013 | Allen, IV et al. |
| 2013/0296923 A1 | 11/2013 | Twomey et al. |
| 2013/0304058 A1 | 11/2013 | Kendrick |
| 2013/0304059 A1 | 11/2013 | Allen, IV et al. |
| 2013/0304066 A1 | 11/2013 | Kerr et al. |
| 2013/0310832 A1 | 11/2013 | Kerr et al. |
| 2013/0325057 A1 | 12/2013 | Larson et al. |
| 2013/0331837 A1 | 12/2013 | Larson |
| 2013/0338666 A1 | 12/2013 | Bucciaglia et al. |
| 2013/0338693 A1 | 12/2013 | Kerr et al. |
| 2013/0345701 A1 | 12/2013 | Allen, IV et al. |
| 2013/0345706 A1 | 12/2013 | Garrison |
| 2013/0345735 A1 | 12/2013 | Mueller |
| 2014/0005663 A1 | 1/2014 | Heard et al. |
| 2014/0005666 A1 | 1/2014 | Moua et al. |
| 2014/0025052 A1 | 1/2014 | Nau, Jr. et al. |
| 2014/0025053 A1 | 1/2014 | Nau, Jr. et al. |
| 2014/0025059 A1 | 1/2014 | Kerr |
| 2014/0025060 A1 | 1/2014 | Kerr |
| 2014/0025066 A1 | 1/2014 | Kerr |
| 2014/0025067 A1 | 1/2014 | Kerr et al. |
| 2014/0025070 A1 | 1/2014 | Kerr et al. |
| 2014/0025073 A1 | 1/2014 | Twomey et al. |
| 2014/0031821 A1 | 1/2014 | Garrison |
| 2014/0031860 A1 | 1/2014 | Stoddard et al. |
| 2014/0046323 A1 | 2/2014 | Payne et al. |
| 2014/0066910 A1 | 3/2014 | Nau, Jr. |
| 2014/0066911 A1 | 3/2014 | Nau, Jr. |
| 2014/0074091 A1 | 3/2014 | Arya et al. |
| 2014/0100564 A1 | 4/2014 | Garrison |
| 2014/0100568 A1 | 4/2014 | Garrison |
| 2014/0135758 A1 | 5/2014 | Mueller |
| 2014/0135763 A1 | 5/2014 | Kappus et al. |
| 2014/0276797 A1 | 9/2014 | Batchelor et al. |

(56) References Cited

U.S. PATENT DOCUMENTS

FOREIGN PATENT DOCUMENTS

| | | |
|---|---|---|
| CN | 201299462 | 9/2009 |
| CN | 101636120 A | 1/2010 |
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 4242143 A1 | 6/1994 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 20 2007 009317 U1 | 8/2007 |
| DE | 202007009165 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| EP | 1530952 | 5/2005 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350703 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/045589 | 6/2002 |
| WO | 02/45589 A2 | 6/2002 |
| WO | 2005/110264 A2 | 11/2005 |
| WO | 2006021269 A1 | 3/2006 |
| WO | 05110264 A3 | 4/2006 |
| WO | 2007118608 A1 | 10/2007 |
| WO | 08/040483 A1 | 4/2008 |
| WO | 2011/018154 A1 | 2/2011 |

OTHER PUBLICATIONS

U.S. Appl. No. 09/177,950, Randel A. Frazier.
U.S. Appl. No. 09/387,883, Dale F. Schmaltz.
U.S. Appl. No. 09/591,328, Thomas P. Ryan.
U.S. Appl. No. 12/336,970, Paul R. Sremeich.
Michael Choti, "Abdominoperineal Resection with the LigaSure Vessel Sealing System and LigaSure Atlas 20 cm Open Instrument"; Innovations That Work, Jun. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).
E. David Crawford "Evaluation of a New Vessel Sealing Device in Urologic Cancer Surgery", 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. TT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.

(56) References Cited

OTHER PUBLICATIONS

Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room", 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex", 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
European Search Report issued in corresponding application No. 15178545.8 dated Mar. 2, 2016.

\* cited by examiner

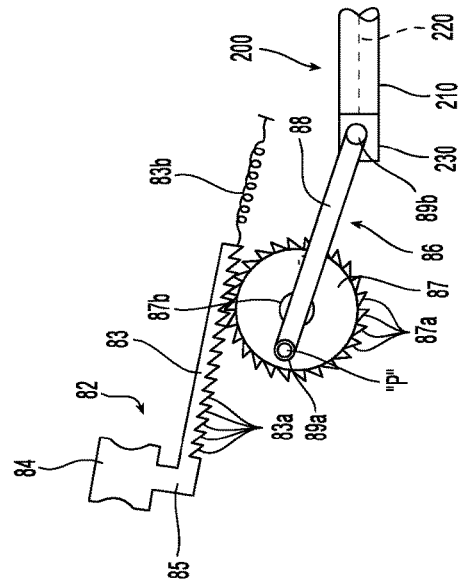
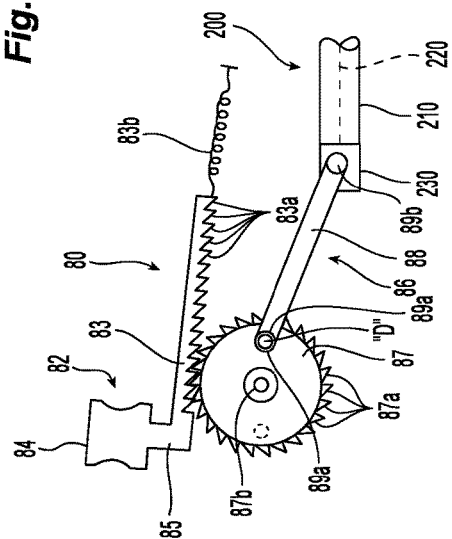
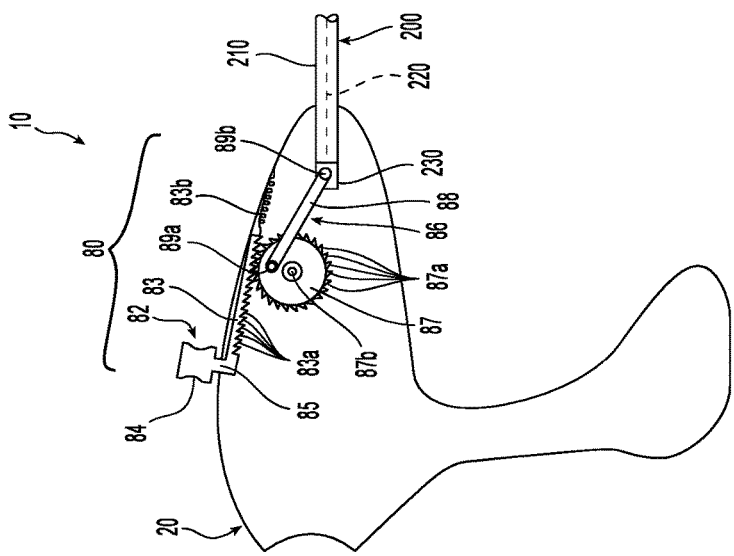
Fig. 7A
Fig. 7B
Fig. 6

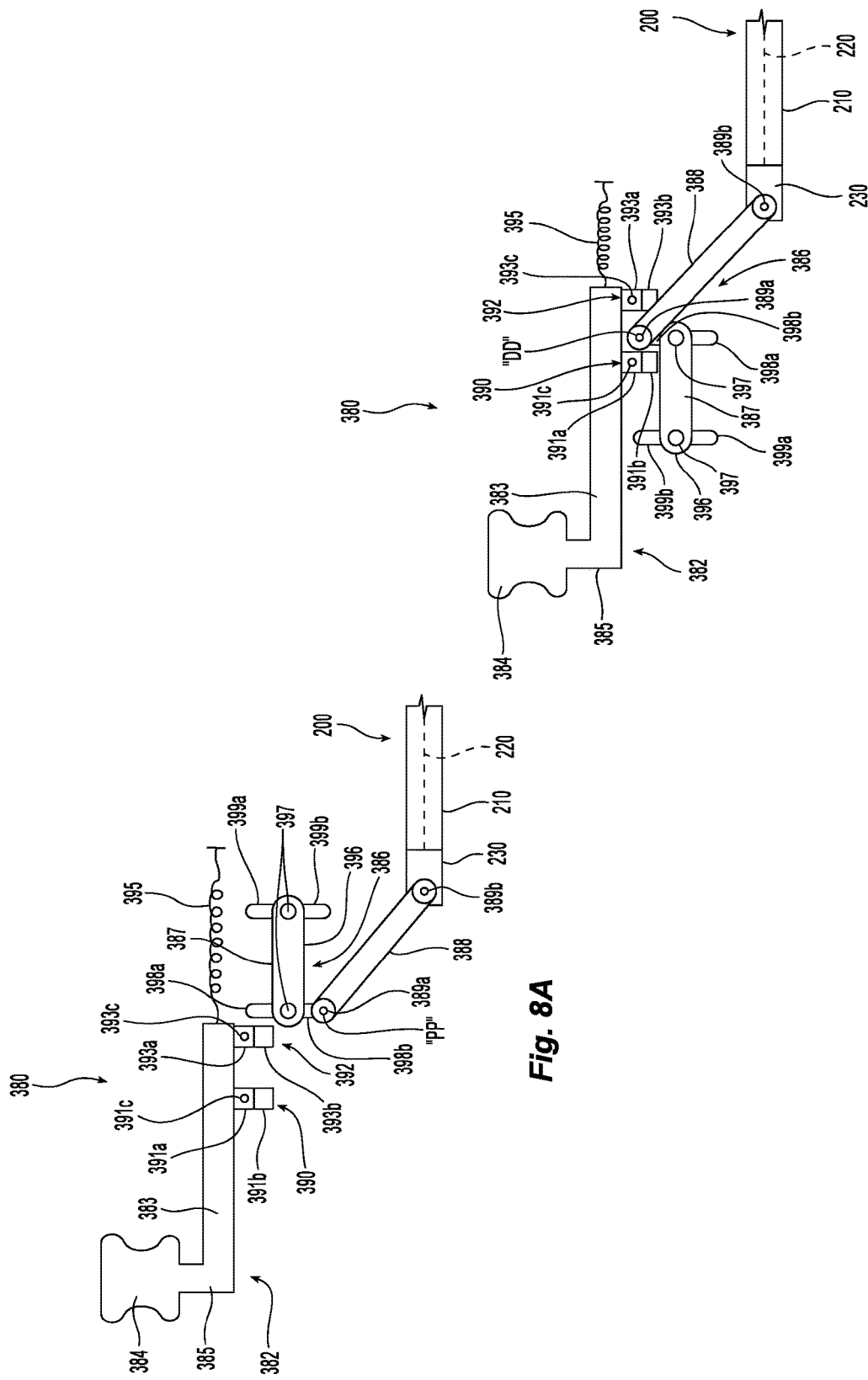

DEPLOYMENT MECHANISMS FOR SURGICAL INSTRUMENTS

CROSS REFERENCES TO RELATED APPLICATION

The present application claims the benefit of and priority to U.S. Provisional Application No. 62/051,394, U.S. Provisional Application No. 62/051,389, and U.S. Provisional Application No. 62/051,391, all of which were filed on Sep. 17, 2014. This application is related to U.S. patent application Ser. No. 14/802,290, and U.S. patent application Ser. No. 14/802,369, both of which were filed on Jul. 17, 2015. The entire contents of each of the above applications are incorporated herein by reference.

BACKGROUND

Technical Field

The present disclosure relates to surgical instruments and, more particularly, to deployment mechanisms for deploying, e.g., actuating, one or more components of a surgical instrument.

Background of Related Art

Many surgical instruments include one or more movable handles, levers, actuators, triggers, etc. for actuating and/or manipulating one or more functional components of the surgical instrument. For example, a surgical forceps may include a movable handle that is selectively compressible relative to a stationary handle for moving first and second jaw members of the forceps between spaced-apart and approximated positions for grasping tissue therebetween. Such a forceps may further include a trigger for selectively deploying a knife between the jaw members to cut tissue grasped therebetween.

As can be appreciated, as additional functional components are added to the surgical instrument, additional deployment structures or deployment structures capable of actuating more than one component are required. However, multiple deployment structures and/or combined deployment structures may be limited by spatial constraints within the housing of the surgical instrument, functional constraints of the components (e.g., where a combined deployment structure imparts additional force requirements for deploying one or more of the components coupled thereto), and/or may overly complicate the operable components of the surgical instrument.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

In accordance with the present disclosure, a surgical instrument is provided including a housing, an energizable member, and a deployment mechanism. The energizable member is movable relative to the housing between a storage position and a deployed position. The deployment mechanism is coupled to the housing and the energizable member and is configured to selectively move the energizable member between the storage position and the deployed position. The deployment mechanism includes a fixed gear operably coupled to the energizable member. The fixed gear is rotatable in a first direction to move the energizable member towards the deployed position and in a second, opposite direction to move the energizable member towards the storage position. The deployment mechanism further includes an actuator assembly including a first actuator and a first gear. The first actuator is movable from an un-actuated position to an actuated position. The actuator assembly is movable relative to the fixed gear between an engaged position, wherein the first gear is disposed in meshed engagement with the fixed gear, and a spaced-apart position, wherein the first gear is spaced-apart from the fixed gear. A reversing assembly is coupled to the housing and includes a second actuator and a second gear. The second actuator is movable between a removed position, wherein the first gear is disposed in the engaged position and the second gear is disengaged from the first gear and the fixed gear, and an inserted position, wherein the first gear is moved to the spaced-apart position and the second gear is engaged between the first gear and the fixed gear.

In an aspect of the present disclosure, movement of the first actuator from the un-actuated position to the actuated position moves the energizable member from the storage position to the deployed position when the second actuator is disposed in the removed position, and movement of the first actuator from the un-actuated position to the actuated position moves the energizable member from the deployed position to the storage position when the second actuator is disposed in the inserted position.

In another aspect of the present disclosure, the first actuator is biased towards the engaged position.

In yet another aspect of the present disclosure, the first actuator is slidable along a slot defined within the housing between the engaged position and the spaced-apart position.

In still another aspect of the present disclosure, the first actuator is rotatable relative to the housing between the un-actuated position and the actuated position.

In still yet another aspect of the present disclosure, the second actuator is translatable relative to the housing between the removed position and the inserted position.

Another surgical instrument provided in accordance with aspects of the present disclosure includes a housing, a shaft extending distally from the housing, an end effector assembly disposed at a distal end of the shaft, a deployable assembly including an energizable member and an insulative member, and a deployment mechanism. The deployable assembly is movable relative to the end effector assembly between a storage position and a deployed position. The deployment mechanism is coupled to the housing and the deployable assembly and is configured to selectively move the deployable assembly between the storage position and the deployed position. The deployment mechanism may include any of the features of any or all of the aspects detailed above.

In an aspect of the present disclosure, the end effector assembly includes first and second jaw members configured to treat tissue in a bipolar mode of operation. Additionally or alternatively, in the deployed position, the insulative member may be disposed about the jaw members with the energizable member extending distally from the jaw members for treating tissue in a monopolar mode of operation.

BRIEF DESCRIPTION OF THE DRAWINGS

Various aspects of the present disclosure are described herein with reference to the drawings wherein like reference numerals identify similar or identical elements:

FIG. 6 is a side view of the proximal end of the forceps of FIG. 1 with a portion of the housing and internal components thereof removed to unobstructively illustrate the proximal end of the monopolar assembly and a deployment mechanism for deploying the monopolar assembly;

FIG. 7A is a side view of the deployment mechanism of FIG. 6 and the proximal end of the monopolar assembly, wherein the deployment mechanism is disposed in an un-actuated condition corresponding to the storage condition of the monopolar assembly;

FIG. 7B is a side view of the deployment mechanism of FIG. 6 and the proximal end of the monopolar assembly, wherein the deployment mechanism is disposed in an actuated condition corresponding to the deployed condition of the monopolar assembly;

FIG. 8A is a side view of another deployment mechanism provided in accordance with the present disclosure and shown coupled to the proximal end of the monopolar assembly, wherein the deployment mechanism is disposed in an un-actuated condition corresponding to the storage condition of the monopolar assembly;

FIG. 8B is a side view of the deployment mechanism of FIG. 8A and the proximal end of the monopolar assembly, wherein the deployment mechanism is disposed in an actuated condition corresponding to the deployed condition of the monopolar assembly;

DETAILED DESCRIPTION

Figure 1:
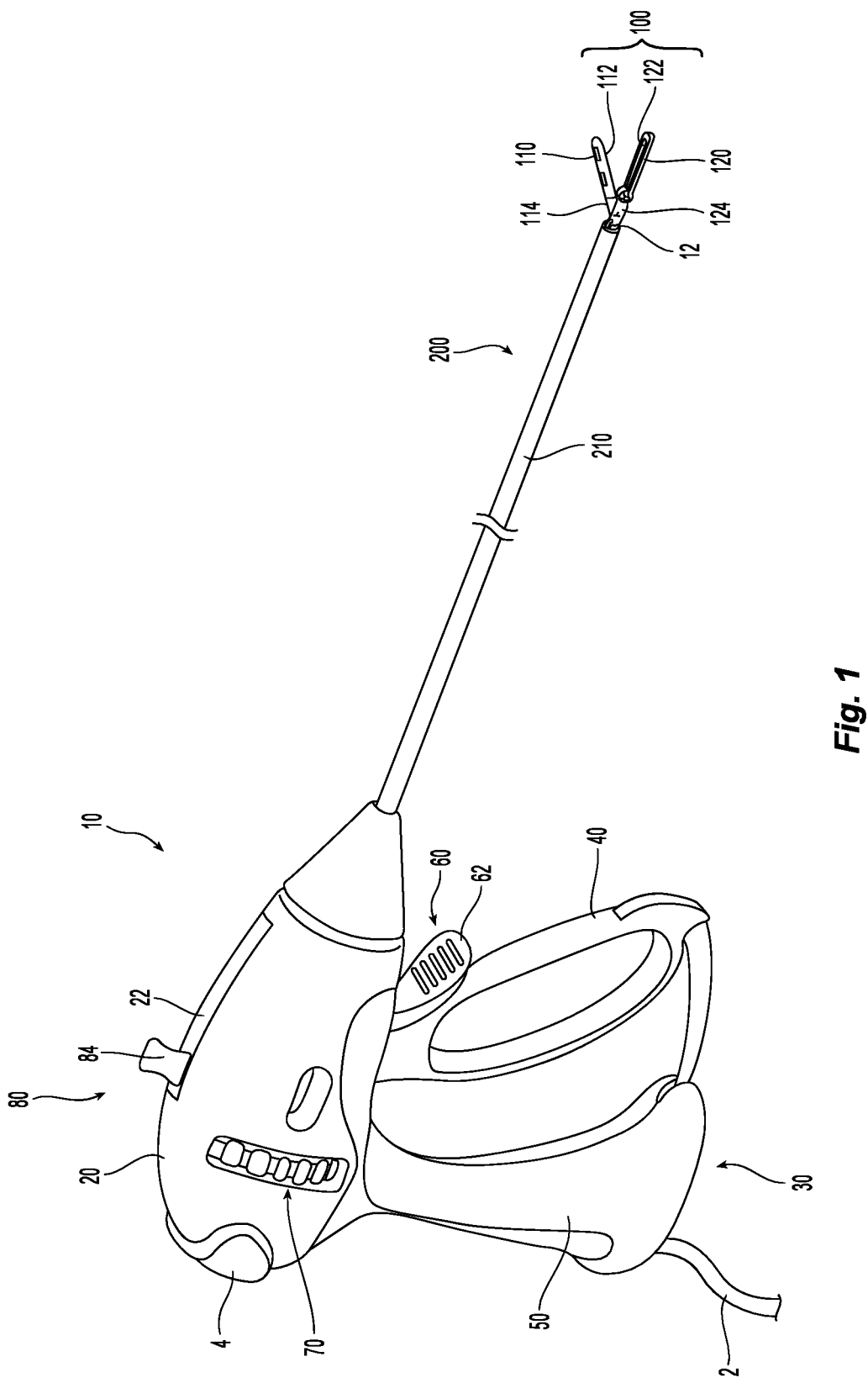
FIG. 1 is a front, perspective view of an endoscopic surgical forceps configured for use in accordance with the present disclosure.

Referring generally to FIG. 1, a forceps provided in accordance with the present disclosure is shown generally identified by reference numeral 10. Forceps 10, as will be described below, is configured to operate in both a bipolar mode, e.g., for grasping, treating, and/or dissecting tissue, and a monopolar mode, e.g., for treating and/or dissecting tissue. Although the present disclosure is shown and described with respect to forceps 10, the aspects and features of the present disclosure are equally applicable for use with any suitable surgical instrument or portion(s) thereof for selectively actuating, moving, and/or deploying one or more assemblies and/or components of the surgical instrument. Obviously, different connections and considerations apply to each particular instrument and the assemblies and/or components thereof; however, the aspects and features of the present disclosure remain generally consistent regardless of the particular instrument, assemblies, and/or components provided.

Continuing with reference to FIG. 1, forceps 10 includes a housing 20, a handle assembly 30, a trigger assembly 60, a rotating assembly 70, a deployment mechanism 80, an end effector assembly 100, and a monopolar assembly 200. Forceps 10 further includes a shaft 12 having a distal end configured to mechanically engage end effector assembly 100 and a proximal end that mechanically engages housing 20. Forceps 10 also includes an electrosurgical cable 2 that connects forceps 10 to a generator (not shown) or other suitable power source, although forceps 10 may alternatively be configured as a battery powered instrument. Cable 2 includes wires (not shown) extending therethrough that have sufficient length to extend through shaft 12 in order to provide electrical energy to at least one of the electrically-conductive surfaces 112, 122 (FIG. 2) of jaw members 110, 120, respectively, of end effector assembly 100, e.g., upon activation of activation switch 4 in a bipolar mode. One or more of the wires (not shown) of cable 2 extends through housing 20 in order to provide electrical energy to monopolar assembly 200, e.g., upon activation of activation switch 4 in a monopolar mode. Rotating assembly 70 is rotatable in either direction to rotate end effector assembly 100 and monopolar assembly 200 relative to housing 20. Housing 20 houses the internal working components of forceps 10.

Figure 2:
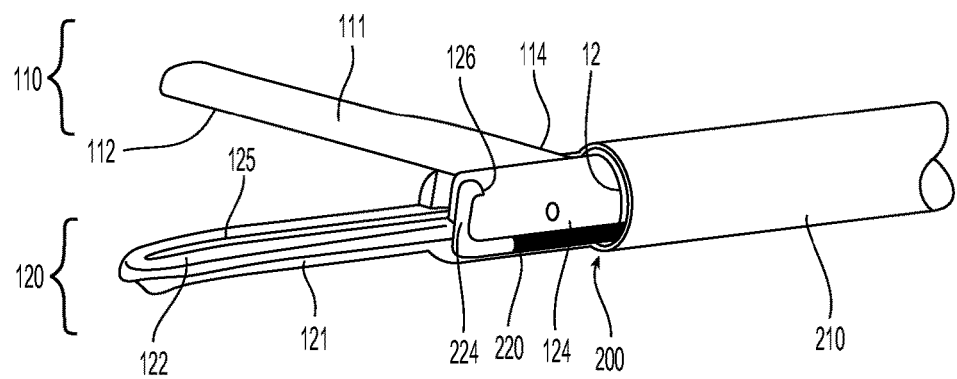
FIG. 2 is an enlarged, front, perspective view of an end effector assembly of the forceps of FIG. 1, wherein jaw members of the end effector assembly are disposed in a spaced-apart position and wherein a monopolar assembly is disposed in a storage condition.
Figure 3:
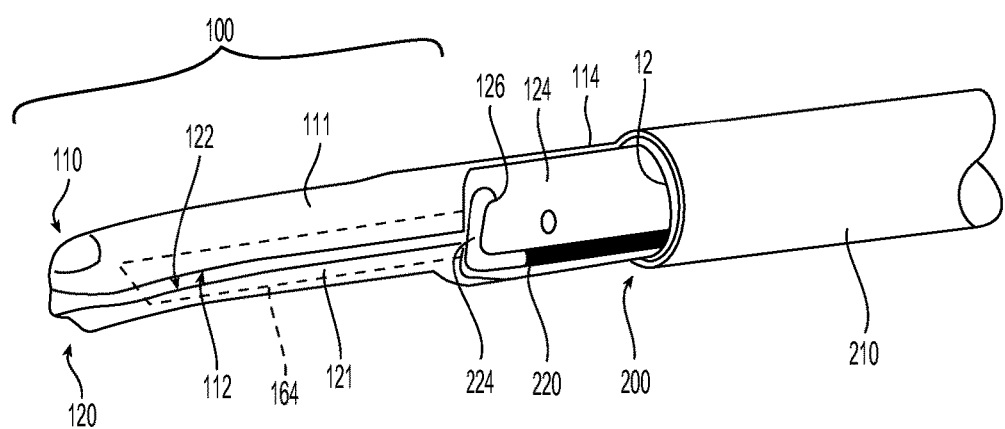
FIG. 3 is an enlarged, front, perspective view of the end effector assembly of FIG. 2, wherein the jaw members are disposed in an approximated position and wherein the monopolar assembly is disposed in the storage condition.
Figure 4:
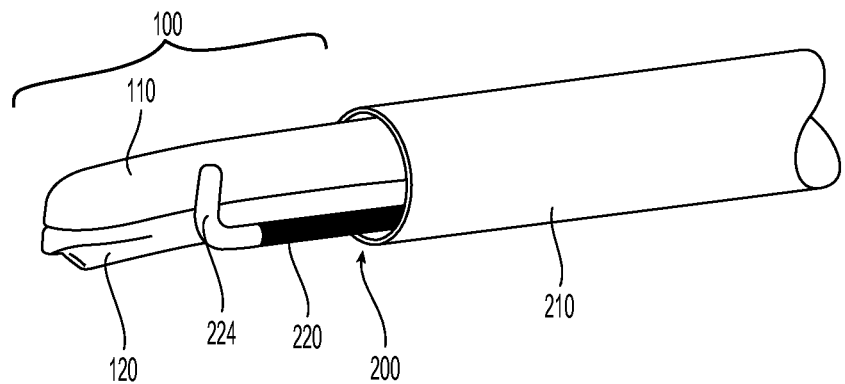
FIG. 4 is an enlarged, front, perspective view of the end effector assembly of FIG. 2, wherein the jaw members are disposed in the approximated position and wherein the monopolar assembly is transitioning from the storage condition to a deployed condition.

Referring to FIGS. 2-3, end effector assembly 100 is attached at the distal end of shaft 12 and includes opposing jaw members 110, 120 pivotably coupled to one another. Each of the jaw members 110 and 120 includes a jaw body 111, 121 supporting the respective electrically-conductive surface 112, 122, and a respective proximally-extending jaw flange 114, 124. Flanges 114, 124 are pivotably coupled to one another to permit movement of jaw members 110, 120 relative to one another between a spaced-apart position (FIG. 2) and an approximated position (FIG. 3) for grasping tissue between surfaces 112, 122. One or both of surfaces 112, 122 are adapted to connect to a source of energy (not explicitly shown), e.g., via the wires (not shown) of cable 2 (FIG. 1), and are configured to conduct energy through tissue grasped therebetween to treat, e.g., seal, tissue. More specifically, in some embodiments, end effector assembly 100 defines a bipolar configuration wherein surface 112 is charged to a first electrical potential and surface 122 is charged to a second, different electrical potential such that an electrical potential gradient is created for conducting energy between surfaces 112, 122 and through tissue grasped therebetween for treating e.g., sealing, tissue. Activation switch 4 (FIG. 1) is operably coupled between the source of energy (not shown) and surfaces 112, 122, thus allowing the user to selectively apply energy to surfaces 112, 122 of jaw members 110, 120, respectively, of end effector assembly 100 during a bipolar mode of operation.

End effector assembly 100 is designed as a unilateral assembly, i.e., where jaw member 120 is fixed relative to shaft 12 and jaw member 110 is movable relative to shaft 12 and fixed jaw member 120. However, end effector assembly 100 may alternatively be configured as a bilateral assembly, i.e., where both jaw member 110 and jaw member 120 are movable relative to one another and to shaft 12. In some embodiments, a knife channel 125 may be defined within one or both of jaw members 110, 120 to permit reciprocation of a knife 164 (FIG. 3) therethrough, e.g., upon actuation of a trigger 62 of trigger assembly 60, to cut tissue grasped between jaw members 110, 120.

Figure 5:
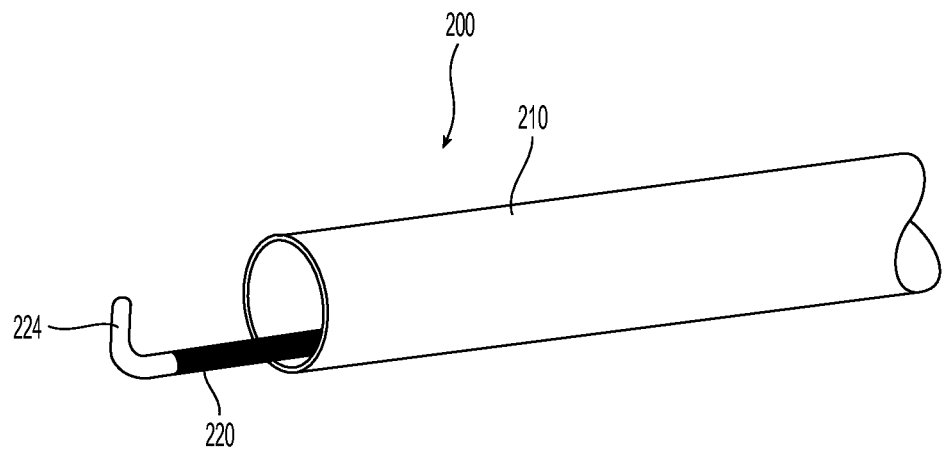
FIG. 5 is an enlarged, front, perspective view of the end effector assembly of FIG. 2, wherein the monopolar assembly is disposed in the deployed condition.

Referring to FIGS. 1-5, monopolar assembly 200 includes an insulative sleeve 210, an energizable rod member 220, and a proximal hub 230 (FIG. 6). Insulative sleeve 210 is slidably disposed about shaft 12 and is selectively movable about and relative to shaft 12 and end effector assembly 100 between a storage position (FIGS. 2 and 3), wherein insulative sleeve 210 is disposed proximally of end effector assembly 100, and a deployed position (FIG. 5), wherein insulative sleeve 210 is substantially disposed about end effector 100 so as to electrically insulate surfaces 112, 122 of jaw members 110, 120, respectively. With momentary reference to FIG. 6, proximal hub 230 is engaged to insulative sleeve 210 at the proximal end of insulative sleeve 210 and also engages the proximal end of energizable rod member 220. As detailed below, deployment mechanism 80 is selectively actuatable to translate proximal hub 230 along a translation axis through housing 20 and relative to shaft 12 to thereby move monopolar assembly 200 between its storage and deployed conditions (FIGS. 3 and 5, respectively). The translation axis may be parallel with an axis defined by shaft 12, may be coaxial with the axis of shaft 12, or may be non-parallel relative thereto.

Referring again to FIGS. 1-5, energizable rod member 220 extends from proximal hub 230 (FIG. 6), through sleeve 210, and distally therefrom, ultimately defining an electrically-conductive distal tip 224. Energizable rod member 220 and, more specifically, distal tip 224 thereof, functions as the active electrode of monopolar assembly 200. The one or more wires (not shown) extending from cable 2 through housing 20 (see FIG. 1), are coupled to energizable rod member 220 to provide energy to energizable rod member 220, e.g., upon actuation of activation switch 4 (FIG. 1) in a monopolar mode, for treating tissue in a monopolar mode of operation. Energizable rod member 220 is movable between a storage position (FIG. 3) and a deployed position (FIG. 5). In the storage position (FIG. 3), distal tip 224 of rod member 220 is disposed within an insulated groove 126 defined within flange 124 of jaw member 120, although other configurations are also contemplated, e.g., distal tip 224 of rod member 220 may simply be positioned alongside flange 124 in the storage condition. Insulated groove 126 electrically-insulates distal tip 224 of rod member 220 from electrically-conductive surfaces 112, 122 of jaw members 110, 120, respectively, e.g., via insulated electrical leads (not explicitly shown) and insulators disposed between surfaces 112, 122 and respective jaw bodies 111, 121, and from surrounding tissue. Alternatively, distal tip 224 of rod member 220 may only be insulated from surface 112 (and is energized to the same potential as surface 122 during use), may only be insulated from surface 122 (and energized to the same potential as surface 112 during use), or may be capable of being energized to the same potential as both surfaces 112, 122 during use.

In the deployed position (FIG. 5), distal tip 224 of rod member 220 of monopolar assembly 200 extends distally from end effector assembly 100 and insulative sleeve 210, which substantially surrounds end effector assembly 100. In this position, energy may be applied to distal tip 224 of rod member 220 to treat tissue, e.g., via activation of activation switch 4 (FIG. 1) in the monopolar mode. Distal tip 224 may be hook-shaped (as shown), or may define any other suitable configuration, e.g., linear, ball, circular, angled, etc.

Insulative sleeve 210 and rod member 220 of monopolar assembly 200 are coupled to one another via a proximal hub 230 (FIG. 6), as will be described in greater detail below, such that insulative sleeve 210 and rod member 220 move in concert with one another between their storage positions (FIGS. 2 and 3), collectively the storage condition of monopolar assembly 200, and their deployed positions (FIG. 5), collectively the deployed condition of monopolar assembly 200, upon selective translation of proximal hub 230 through housing 20 and relative to shaft 12 (see FIG. 1).

With reference again to FIG. 1, handle assembly 30 includes a movable handle 40 and a fixed handle 50. Fixed handle 50 is integrally associated with housing 20 and movable handle 40 is movable relative to fixed handle 50. Movable handle 40 is movable relative to fixed handle 50 between an initial position, wherein movable handle 40 is spaced from fixed handle 50, and a compressed position, wherein movable handle 40 is compressed towards fixed handle 50. A biasing member (not shown) may be provided to bias movable handle 40 towards the initial position. Movable handle 40 is ultimately connected to a drive assembly (not shown) disposed within housing 20 that, together, mechanically cooperate to impart movement of jaw members 110, 120 between the spaced-apart position (FIG. 2), corresponding to the initial position of movable handle 40, and the approximated position (FIG. 3), corresponding to the compressed position of movable handle 40. Any suitable drive assembly for this purpose may be provided such as, for example, the drive assembly disclosed in U.S. patent application Ser. No. 14/052,871, filed on Oct. 14, 2013, the entire contents of which are incorporated herein by reference.

Trigger assembly 60 includes trigger 62 that is operably coupled to knife 164 (FIG. 3). Trigger 62 of trigger assembly 60 is selectively actuatable to advance knife 164 (FIG. 3) from a retracted position, wherein knife 164 (FIG. 3) is disposed proximally of jaw members 110, 120, to an extended position, wherein knife 164 (FIG. 3) extends at least partially between jaw members 110, 120 and through knife channel(s) 125 (FIG. 2) to cut tissue grasped between jaw members 110, 120.

Detailed below with respect to FIGS. 6-15 are various embodiments of deployment mechanisms for selectively deploying monopolar assembly 200 (or similar monopolar assemblies). To the extent consistent, the various deployment mechanisms, although described separately, may include any or all of the features of any or all of the other deployment mechanisms.

Referring to FIGS. 6-7B, deployment mechanism 80 is configured for selectively translating proximal hub 230 relative to housing 20 and shaft 12 (FIG. 1) to thereby transition monopolar assembly 200 between its storage condition (FIGS. 2 and 3) and its deployed condition (FIG. 5). Deployment mechanism 80 generally includes an actuator member 82 coupled to a ratchet and linkage assembly 86 for selectively deploying monopolar assembly 200 in a push-push fashion, that is, where deployment of monopolar assembly 200 is effected via a first actuation of deployment mechanism 80 and where retraction of monopolar assembly 200 is effected via a second, subsequent actuation of deployment mechanism.

Actuator member 82 includes a rack 83, an actuator 84, and a post 85 extending between and interconnecting rack 83 with actuator 84. Rack 83 is disposed within housing 20, while post 85 extends through a slot 22 (FIG. 1) defined within housing 20 to permit manipulation of actuator 84 from the exterior of housing 20. Rack 83 further defines a plurality of teeth 83a disposed in longitudinal arrangement along rack 83. A biasing member 83b is coupled to rack 83 so as to bias rack proximally relative to housing 20, thereby biasing actuator 84 towards the proximal end of slot 22 (see FIG. 1). Although biasing member 83b is shown coupled to the distal end of rack 83 functioning as a compression spring, it is also envisioned that biasing member 83b be coupled to the proximal end of rack 83 to act as an extension spring, or that any other suitable biasing member and/or configuration thereof be provided.

Ratchet and linkage assembly 86 includes a ratchet wheel 87 rotatably coupled to housing 20 and a linkage bar 88 pivotably coupled to ratchet wheel 87 at an eccentric position, e.g., at a position offset from the rotation axis of ratchet wheel 87. Ratchet wheel 87 includes a plurality of teeth 87a circumferentially disposed about the outer peripheral surface thereof, and is positioned in meshed engagement with rack 83. More specifically, teeth 87a of ratchet wheel 87 and teeth 83a of rack 83 are configured and oriented such that, upon distal translation of rack 83 relative to ratchet wheel 87, teeth 83a engage teeth 87a to urge ratchet wheel 87 to rotate in a clockwise direction (as viewed from the orientation shown in FIGS. 6-7B) and such that, upon proximal translation of rack 83 relative to ratchet wheel 87, teeth 83a cam along and over teeth 87a without effecting rotation of ratchet wheel 87. Thus, ratchet wheel 87 is an unlimited, one-way rotatable member in that it is rotatable in one direction, e.g., clockwise direction (as viewed from the orientation shown in FIGS. 6-7B), and is not limited in its degree of rotation or number of rotations.

Continuing with reference to FIGS. 6-7B, linkage bar 88 includes a first end 89a that, as mentioned above, is pivotably coupled to ratchet wheel 87 at an eccentric position relative to the rotation axis of ratchet wheel 87. As such, upon rotation of ratchet wheel 87, first end 89a of linkage bar 88 orbits about the rotation axis of ratchet wheel 87, urging linkage bar 88 more proximally or more distally, depending on the position of first end 89a of linkage bar 88. Linkage bar 88 further includes a second end 89b that is pivotably coupled to proximal hub 230 of monopolar assembly 200. Thus, depending on the position of first end 89a of linkage bar 88 in orbit about the rotation axis of ratchet wheel 87, rotation of ratchet wheel 87 effects either distal translation of monopolar assembly 200, e.g., towards the deployed condition, or proximal translation of monopolar assembly 200, e.g., towards the storage condition. A dual biasing mechanism 87b, e.g., one or more springs, a clutch, or other suitable mechanism, is coupled to ratchet wheel 87 and provided to establish a bi-stable configuration of ratchet wheel 87; that is, where ratchet wheel 87 is biased towards both a first rotational orientation, wherein first end 89a of linkage bar 88 is disposed in a proximal position "P" (FIG. 7A), and an opposite, second rotational orientation, wherein first end 89a of linkage bar 88 is disposed in a distal position "D" (FIG. 7B). The use and operation of deployment mechanism 80 for selectively deploying and retracting monopolar assembly 200 is detailed below.

Referring to FIGS. 1-3 and 7A, initially, actuator 84 is disposed at the proximal end of slot 22 defined within housing 20, first end 89a of linkage bar 88 is positioned proximally of the rotation axis of ratchet wheel 87 at proximal position "P," and, accordingly, monopolar assembly 200 is disposed in the storage condition. In order to deploy monopolar assembly 200, actuator 84 of actuator member 82 is translated distally along slot 22 and against the bias of biasing member 83b towards the distal end of slot 22. As actuator member 82 is translated in this manner, teeth 83a of rack 83 of actuator member 82 engage teeth 87a of ratchet wheel 87 to urge ratchet wheel 87 to rotate in a clockwise direction (as viewed from the orientation shown in FIGS. 7A and 7B), such that first end 89a of linkage bar 88 is moved from the proximal position "P" to the distal position "D." Such movement of first end 89a of linkage bar 88 urges linkage bar 88 distally which, in turn, urges proximal hub 230 distally such that insulative sleeve 210 and rod member 220 are transitioned from their respective storage positions (FIGS. 2 and 3), through intermediate positions (FIG. 4), and ultimately, to their respective deployed positions (FIG. 5).

As mentioned above, dual biasing mechanism 87b establishes a bi-stable configuration of ratchet wheel 87. Thus, where an insufficient distal advancement of actuator 84 is effected, e.g., less than 50% actuation, dual biasing mechanism 87b operates to return ratchet wheel 87 to the first rotational orientation, wherein first end 89a of linkage bar 88 is disposed in the proximal position "P" (FIG. 7A) and monopolar assembly 200 is disposed in the storage condition (FIGS. 2 and 3). On the other hand, upon sufficient but less than full distal advancement of actuator 84, e.g., greater than 50% actuation, dual biasing mechanism 87b operates to further urge ratchet wheel 87 to the second rotational orientation, wherein first end 89a of linkage bar 88 is disposed in the distal position "D" (FIG. 7B) and monopolar assembly 200 is disposed in the deployed condition (FIG. 5). Other suitable mechanisms for retaining and maintaining monopolar assembly 200 in the storage and/or deployed conditions are also contemplated, for example, detents, latches, etc. may be provided to stop and hold monopolar assembly 200 at 180 degree intervals of rotation of ratchet wheel 87.

Once sufficiently actuated, actuator 84 may be released. Upon release of actuator 84, biasing member 83b urges rack 83 and actuator 84 proximally while teeth 83a cam along and over teeth 87a such that actuator member 82 is returned proximally to its initial position while ratchet wheel 87 is maintained in (or further rotated under bias of dual biasing mechanism 87b to) the second orientation, wherein first end 89a of linkage bar 88 is disposed in the distal position "D" (FIG. 7B) and monopolar assembly 200 is disposed in the deployed condition (FIG. 5).

At this point, actuator 84 is disposed at the proximal end of slot 22 defined within housing 20, ratchet wheel 87 is disposed in the second rotational orientation, and monopolar assembly 200 is disposed in the deployed condition. In order to return monopolar assembly 200 to the storage condition, actuator 84 is once again translated distally along slot 22 and against the bias of biasing member 83b towards the distal end of slot 22. As actuator member 82 is translated distally, teeth 83a of rack 83 of actuator member 82 engage teeth 87a of ratchet wheel 87 to urge ratchet wheel 87 to rotate in a clockwise direction (as viewed from the orientation shown in FIGS. 7A and 7B), such that first end 89a of linkage bar 88 is moved from the distal position "D" back to the proximal position "P." Such movement of first end 89a of linkage bar 88 pulls linkage bar 88 proximally which, in turn, pulls proximal hub 230 proximally such that insulative sleeve 210 and rod member 220 are transitioned from their respective deployed positions (FIG. 5), through intermediate positions (FIG. 4), and ultimately, to their respective storage positions (FIGS. 2 and 3), e.g., the storage condition of monopolar assembly 200.

Once sufficiently actuated as detailed above, actuator 84 may be released. Upon release of actuator 84, biasing member 83b urges rack 83 and actuator 84 proximally while teeth 83a cam along and over teeth 87a such that actuator member 82 is returned proximally to its initial position while ratchet wheel 87 is maintained in (or further rotated under bias of dual biasing mechanism 87b to) the first orientation, wherein first end 89a of linkage bar 88 is disposed in the proximal position "P" (FIG. 7A) and monopolar assembly 200 is disposed in the storage condition (FIGS. 2 and 3). Re-deployment and retraction of monopolar assembly 200 may subsequently be achieved similarly as detailed above.

Referring to FIGS. 1-7B, the use and operation of forceps 10 in both the bipolar mode, e.g., for grasping, treating (for example, sealing), and/or cutting tissue, and the monopolar mode, e.g., for electrical/electromechanical tissue treatment, is described. Turning to FIGS. 1 and 2, with respect to use in the bipolar mode, monopolar assembly 200 is maintained in the storage condition, wherein insulative sleeve 210 is positioned proximally of jaw members 110, 120, and distal tip 224 of energizable rod member 220 is disposed within insulative groove 126 of jaw flange 124 of jaw member 120. At this point, movable handle 40 is disposed in its initial position such that jaw members 110, 120 are disposed in the spaced-apart position. Further, trigger 62 of trigger assembly 60 remains un-actuated such that knife 164 (FIG. 3) remains disposed in its retracted position.

Continuing with reference to FIGS. 1 and 2, with jaw members 110, 120 disposed in the spaced-apart position (FIG. 2), end effector assembly 100 may be maneuvered into position such that tissue to be grasped, treated, e.g., sealed, and/or cut, is disposed between jaw members 110, 120. Next, movable handle 40 is depressed, or pulled proximally relative to fixed handle 50 such that jaw member 110 is pivoted relative to jaw member 120 from the spaced-apart position to the approximated position to grasp tissue therebetween, as shown in FIG. 3. In this approximated position, energy may be supplied, e.g., via activation of switch 4, to plate 112 of jaw member 110 and/or plate 122 of jaw member 120 and conducted through tissue to treat tissue, e.g., to effect a tissue seal or otherwise treat tissue in the bipolar mode of operation. Once tissue treatment is complete (or to cut untreated tissue), knife 164 (FIG. 3) may be deployed from within shaft 12 to between jaw members 110, 120, e.g., via actuation of trigger 62 of trigger assembly 60, to cut tissue grasped between jaw members 110, 120.

When tissue cutting is complete, trigger 62 may be released to return knife 164 (FIG. 3) to the retracted position. Thereafter, movable handle 40 may be released or returned to its initial position such that jaw members 110, 120 are moved back to the spaced-apart position (FIG. 2) to release the treated and/or divided tissue.

Referring to FIGS. 1 and 3-7B, for operation of forceps 10 in the monopolar mode, jaw members 110, 120 are first moved to the approximated position, e.g., by depressing movable handle 40 relative to fixed handle 50. A lockout mechanism for inhibiting deployment of monopolar assembly 200 prior to movement of jaw members 110, 120 to the approximated positions may also be provided, such as the lockout mechanism described in U.S. patent application Ser. No. 14/276,465, filed on May 13, 2014, the entire contents of which are incorporated herein by reference. Once the approximated position has been achieved, monopolar assembly 200 may be deployed by transitioning deployment mechanism 80 from the un-actuated condition to the actuated condition. More specifically, in order to deploy monopolar assembly 200, actuator 84 is translated distally along slot 22 from the position shown in FIG. 7A to the position shown in FIG. 7B. This initial distal translation of actuator 84, as detailed above, urges proximal hub 230 distally relative to housing 20 and shaft 12 and, as a result, moves insulative sleeve 210 and energizable rod member 220 distally from their respective storage positions (FIGS. 2 and 3) to their respective deployed positions (FIG. 5), e.g., the deployed condition of monopolar assembly 200.

With monopolar assembly 200 disposed in the deployed condition, actuator 84 may be released such that actuator 84 is returned to its initial, proximal position while monopolar assembly 200 is maintained in the deployed condition. Thereafter, activation switch 4 may be actuated to supply energy to energizable rod member 220 to treat, e.g., dissect or otherwise treat, tissue. During application of energy to tissue via energizable rod member 220, forceps 10 may be moved relative to tissue, e.g., longitudinally, transversely, and/or radially, to facilitate electromechanical treatment of tissue. At the completion of tissue treatment, actuator 84 may be actuated a subsequent time, e.g., actuator 84 may once again be translated distally along slot 22. Due to the configuration of deployment mechanism 80, this second, subsequent actuation of actuator 84 pulls proximal hub 230 proximally relative to housing 20 and shaft 12 and, as a result, pulls insulative sleeve 210 and energizable rod member 220 proximally from their respective deployed positions (FIG. 5) back to their respective storage positions (FIGS. 2 and 3), e.g., the storage condition of monopolar assembly 200. Once the storage condition of monopolar assembly 200 has been achieved, actuator 84 may be released, allowing actuator 84 to return to its initial position at the proximal end of slot 22.

Turning now to FIGS. 8A and 8B, another embodiment of a deployment mechanism for selectively deploying and retracting monopolar assembly 200 in a push-push manner is shown designated as deployment mechanism 380. Deployment mechanism 380 generally includes an actuator member 382 coupled to a conveyor and linkage assembly 386. Actuator member 382 includes a shaft 383, an actuator 384, and a post 385 extending between and interconnecting a first end of shaft 383 with actuator 384. Post 385 is configured to extend through slot 22 of housing 20 (see FIG. 1) to permit manipulation of actuator 384 from the exterior of housing 20 (FIG. 1). A biasing member 395 is coupled to shaft 383 so as to bias shaft 383 proximally relative to housing 20 (FIG. 1), although other configurations are also contemplated.

Shaft 383 of actuator member 382 includes first and second hinge fingers 390, 392 extending therefrom towards the second, opposite end of shaft 383. Hinge fingers 390, 392 each include a first segment 391a, 393a that is fixedly engaged to shaft 383 and a second segment 391b, 393b that is pivotably coupled to the respective first segments 391a, 393a via a one-way hinge 391c, 393c. One-way hinges 391c, 393c are configured to permit second segments 391b, 393b to pivot distally (counterclockwise from the orientation shown in FIGS. 8A and 8B) relative to first segments 391a, 393a from an aligned position, wherein the first and second segments 391a, 391b and 393a, 393b of each respective hinge finger 390, 392 cooperates to define a generally linear configuration. One-way hinges 391c, 393c are further configured to inhibit second segments 391b, 393b from pivoting proximally (clockwise from the orientation shown in FIGS. 8A and 8B) relative to first segments 391a, 393a from the aligned position. As an alternative to providing one-way hinges 391c, 393c, fingers 390, 392 and the fingers 398a, 398b and 399a, 399b of conveyor and linkage assembly 386 may define gear-teeth configurations similar to those of rack 83 and ratchet wheel 87 (FIGS. 7A and 7B), e.g., wherein the teeth engage one another when moved in a first direction and cam over one another when moved in a second direction. Other suitable configurations are also contemplated.

Conveyor and linkage assembly 386 includes a conveyor 387 and a linkage bar 388. Conveyor 387 includes a belt 396 rotatable about a pair of spaced-apart pivots 397. Similar to ratchet wheel 87 (FIGS. 7A and 7), belt 396 is an unlimited, one-way rotatable member in that it is rotatable in one direction, e.g., clockwise direction (as viewed from the orientation shown in FIGS. 8A and 8B), and is not limited in its degree of rotation or number of rotations. Two pairs of spaced-apart fingers 398a, 398b and 399a, 399b are disposed on belt 396 at opposing locations. Linkage bar 388 is pivotably coupled to one of the fingers, e.g., finger 398b, at a first end 389a of linkage bar 388 and is movable upon rotation of belt 396 between a proximal position "PP" (FIG. 8A) and distal position "DD" (FIG. 8B). Second end 389b of linkage bar 388 is pivotably coupled to proximal hub 230 of monopolar assembly 200. Thus, upon rotation of belt 396 about pivots 397, first end 389a of linkage bar 388 is orbited in an oval-shaped orbit between the proximal position "PP" and the distal position "DD," urging linkage bar 388 more proximally or more distally, depending on the position of first end 389a of linkage bar 388. Proximal or distal movement of linkage bar 388, in turn, effects either distal translation of monopolar assembly 200, e.g., towards the deployed condition, or proximal translation of monopolar assembly 200, e.g., towards the storage condition. The use and operation of deployment mechanism 380 for selectively deploying and retracting monopolar assembly 200 is detailed below.

Continuing with reference to FIGS. 8A and 8B, initially, actuator 384 is disposed at the proximal end of slot 22 defined within housing 20 (see FIG. 1), first end 389a of linkage bar 388 is disposed at the proximal position "PP" (FIG. 8A) and, accordingly, monopolar assembly 200 is disposed in the storage condition (FIGS. 2 and 3). In order to deploy monopolar assembly 200, actuator 384 is translated distally against the bias of biasing member 383b. As actuator 384 is translated in this manner, hinge fingers 390, 392 contact fingers 398b, 398a, respectively, to urge belt 396 to rotate in a clockwise direction (as viewed from the orientation shown in FIGS. 8A and 8B), such that first end 389a of linkage bar 388 is moved from the proximal position "PP" to the distal position "DD" (FIG. 8B). Such movement of first end 389a of linkage bar 388 urges linkage bar 388 distally which, in turn, urges proximal hub 230 distally such that monopolar assembly 200 is transitioned from the storage condition (FIGS. 2 and 3) to the deployed condition (FIG. 5).

Once actuator 384 has been fully actuated to transition monopolar assembly 200 from the storage condition (FIGS. 2 and 3) to the deployed condition (FIG. 5), actuator 384 may be released. Upon release of actuator 384, biasing member 383b urges shaft 383 and actuator 384 proximally. As shaft 383 is translated proximally, second segments 391b, 393b of hinge fingers 390, 392 contact fingers 399b, 398b and are urged to pivot to permit hinge fingers 390, 392 to pass over fingers 399b, 398b without effecting rotation of belt 396. Thus, actuator member 382 is returned to its initial position, while first end 389a of linkage bar 388 is maintained in the distal position "DD" corresponding to the deployed condition of monopolar assembly 200.

At this point, actuator 384 is once again disposed in its initial position and monopolar assembly 200 is disposed in the deployed condition. In order to return monopolar assembly 200 to the storage condition, actuator 384 is once again actuated, e.g., translated distally against the bias of biasing member 383b. As actuator 384 is translated distally, hinge fingers 390, 392 contact fingers 399b, 399a, respectively, to urge belt 396 to rotate in a clockwise direction (as viewed from the orientation shown in FIGS. 8A and 8B), such that first end 389a of linkage bar 388 is moved from the distal position "DD" back to the proximal position "PP." Such movement of first end 389a of linkage bar 388 pulls linkage bar 388 proximally which, in turn, pulls proximal hub 230 proximally such that monopolar assembly 200 is transitioned from the deployed condition (FIG. 5) back to the storage condition (FIGS. 2 and 3).

Once the second, or subsequent actuation of actuator 384 has been effected to return monopolar assembly 200 to the storage condition (FIGS. 2 and 3), actuator 384 may be released. Upon release of actuator 384, biasing member 383b urges shaft 383 and actuator 384 proximally while second segments 391b, 393b of hinge fingers 390, 392 contact fingers 398a, 399a and are urged to pivot to permit hinge fingers 390, 392 to pass over fingers 398a, 399a without effecting rotation of belt 396. Re-deployment and retraction of monopolar assembly 200 may subsequently be achieved similarly as detailed above. Further, the use and operation of forceps 10 (FIG. 1) with deployment mechanism 380 is similar to that detailed above with respect to deployment mechanism 80 (FIG. 1). Alternatively, belt 396 may be driven by a gear and ratchet mechanism similar to that detailed above with respect to FIGS. 6-7B.

Figure 9:
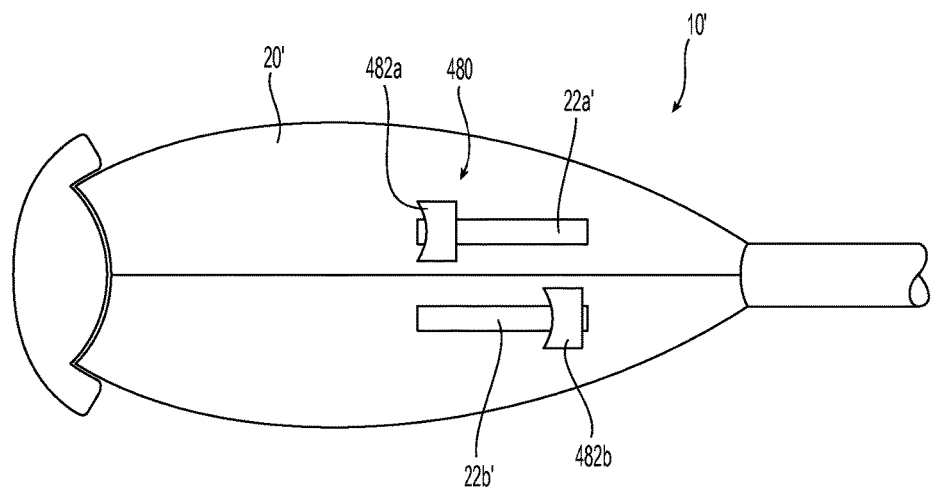
FIG. 9 is a top view of the proximal end of a forceps similar to the forceps of FIG. 1, shown including another deployment mechanism provided in accordance with the present disclosure coupled to the forceps.
Figure 10A:
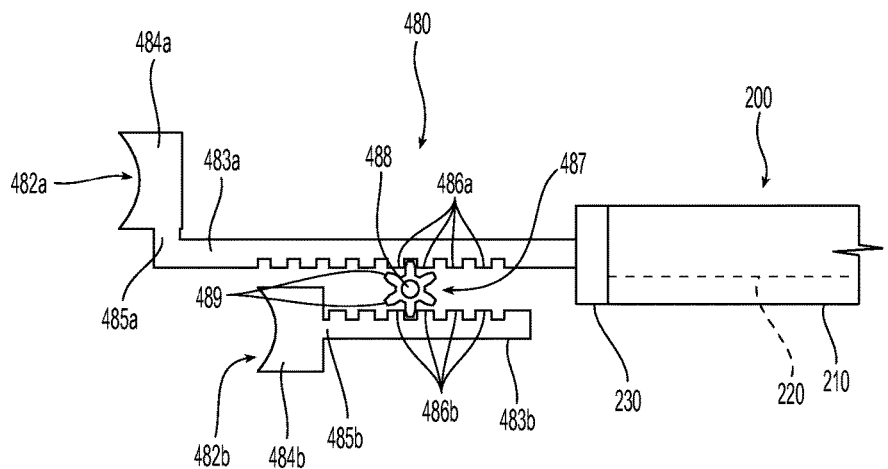
FIG. 10A is a top view of the deployment mechanism of FIG. 9 and the proximal end of the monopolar assembly, wherein the deployment mechanism is disposed in an un-actuated condition corresponding to the storage condition of the monopolar assembly.
Figure 10B:
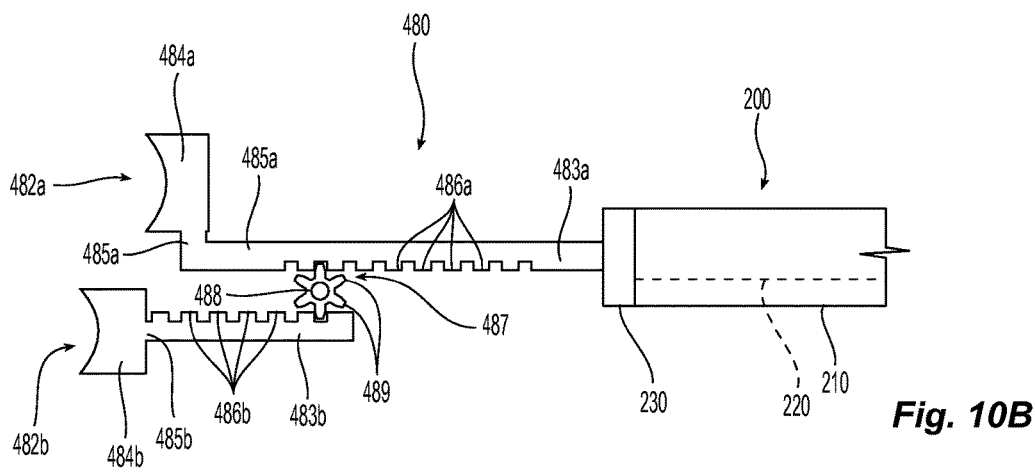
FIG. 10B is a side view of the deployment mechanism of FIG. 9 and the proximal end of the monopolar assembly, wherein the deployment mechanism is disposed in an actuated condition corresponding to the deployed condition of the monopolar assembly.

Turning now to FIGS. 9-10B, another embodiment of a deployment mechanism for selectively deploying and retracting monopolar assembly 200 in a push-push manner is shown designated as deployment mechanism 480. Deployment mechanism 480 is shown configured for use with a forceps 10', which is similar to and may include any or all of the features of forceps 10 (FIG. 1). Forceps 10' differs from forceps 10 (FIG. 1) in the configuration of housing 20'. More specifically, housing 20' of forceps 10' includes first and second longitudinally-extending slots 22a', 22b' defined therethrough. Although slots 22a', 22b' are shown disposed on opposite sides of housing 20', it is envisioned that slots 22a' 22b' may be provided at any suitable location on housing 20'.

Deployment mechanism 480 includes first and second actuator members 482a, 482b extending through respective first and second slots 22a', 22b' of housing 20'. Each actuator member 482a, 482b includes a rack 483a, 483b, an actuator 484a, 484b, and a post 485a, 485b that extends between and interconnects the first end of the respective racks 483a, 483b with the respective actuator 484a, 484b. Posts 485a, 485b extend through respective slots 22a', 22b' of housing 20' to permit manipulation of actuators 484a, 484b from the exterior of housing 20'. Racks 483a, 483b each define a plurality of engagement teeth 486a, 486b, respectively, extending longitudinally therealong. One of the racks, e.g., rack 483a, is engaged to proximal hub 230 of monopolar assembly 200 at the second end of the rack 483a.

Deployment mechanism 480 further includes a gear 487 that is rotatably coupled to housing 20' (FIG. 9) via a pin 488. Gear 487 includes a plurality of teeth 489 circumferentially disposed about the outer peripheral surface thereof. Gear 487 is interdisposed between racks 483a, 483b and positioned such that teeth 489 are disposed in meshed engagement with teeth 486a of rack 483a and teeth 486b of rack 483b. As a result of this configuration, translation of rack 483a in a first direction effects rotation of gear 487 and corresponding translation of rack 483b in a second, opposite direction, and vice versa. More specifically, with monopolar assembly 200 coupled to rack 483a, actuator 484a may be translated distally along slot 22a' of housing 20' to urge monopolar assembly 200 distally towards the deployed condition. On the other hand, actuator 484b may be translated distally along slot 22b' of housing 20' to pull monopolar assembly 200 proximally towards the retracted condition. That is, distal actuation of actuator member 482a effects deployment of monopolar assembly 200, while distal actuation of actuator member 482b effects retraction of monopolar assembly 200. The use and operation of forceps 10' with deployment mechanism 480 is otherwise similar to that detailed above with respect to deployment mechanism 80 and forceps 10 (FIG. 1). Alternatively, deployment mechanism 480 may be replaced with a belt-based system similar to that detailed above with respect to deployment mechanism 380 (FIGS. 8A and 8B) with actuator member 482a, 482b attached to opposing sides of the belt.

Figure 11:
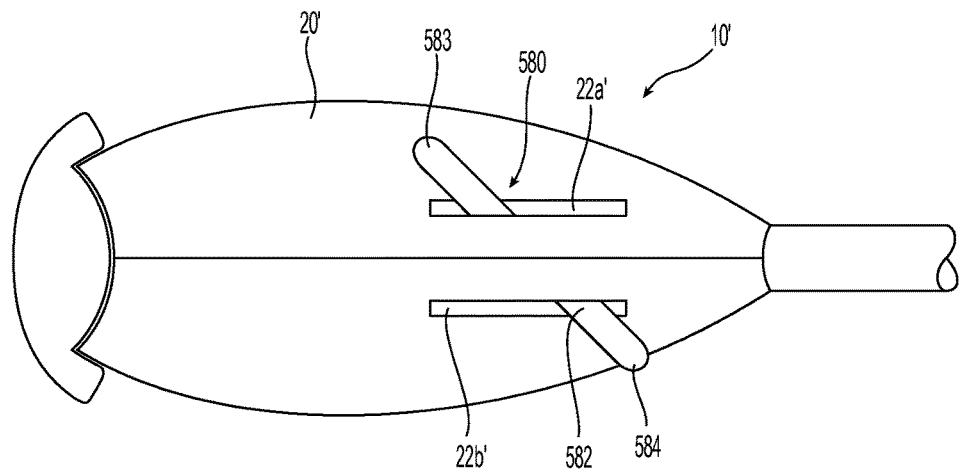
FIG. 11 is a top view of the proximal end of a forceps similar to the forceps of FIG. 1, shown including another deployment mechanism provided in accordance with the present disclosure coupled to the forceps.
Figure 12A:
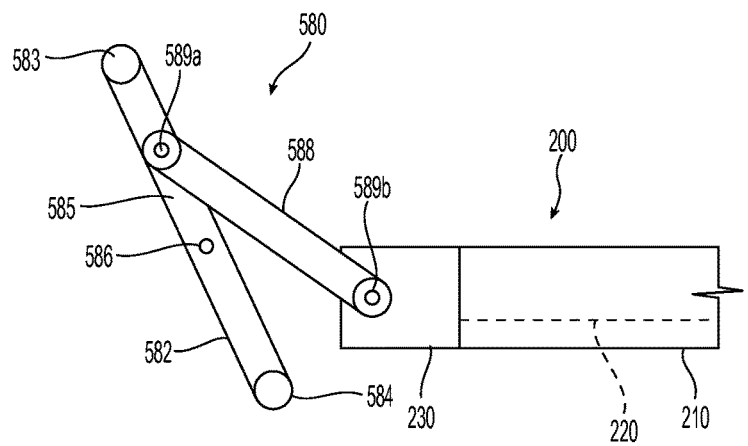
FIG. 12A is a top view of the deployment mechanism of FIG. 11 and the proximal end of the monopolar assembly, wherein the deployment mechanism is disposed in an un-actuated condition corresponding to the storage condition of the monopolar assembly.
Figure 12B:
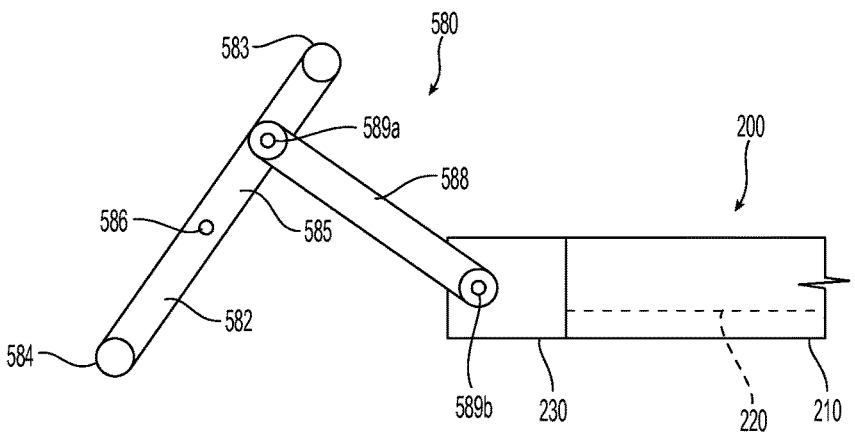
FIG. 12B is a side view of the deployment mechanism of FIG. 11 and the proximal end of the monopolar assembly, wherein the deployment mechanism is disposed in an actuated condition corresponding to the deployed condition of the monopolar assembly.

Turning now to FIGS. 11-12B, another embodiment of a deployment mechanism for selectively deploying and retracting monopolar assembly 200 in a push-push manner is shown designated as deployment mechanism 580. Deployment mechanism 580 is shown configured for use with forceps 10' and generally includes a pivotable actuator member 582 coupled to a linkage bar 588. Actuator member 582 defines a first end 583 that extends through slot 22a' of housing 20', a second end 584 that extends through slot 22b' of housing 20', and an intermediate portion 585 that extends between and interconnects the first and second ends 583, 584 of actuator member 582. Intermediate portion 585 of actuator member 582 is rotatably coupled to housing 20' via a pin 586. First and second ends 583, 584 of actuator member 582 are selectively manipulatable from the exterior of housing 20' to rotate actuator member 582 about pin 586. As can be appreciated, distal urging of first end 583 effects proximal movement of second end 584, and vice versa, due to the positioning of first and second ends 583, 584 of actuator member 582 on opposite sides of pin 586.

Linkage bar 588 includes a first end 589a that is pivotably coupled to actuator member 582 at a position offset relative to pin 586, e.g., between pin 586 and first end 583 of actuator member 582. Second end 589b of linkage bar 588 is pivotably coupled to proximal hub 230 of monopolar assembly 200. As a result of this configuration, distal translation of first end 583 of actuator member 582 along slot 22a' urges linkage bar 588 distally, thereby urging monopolar assembly 200 towards the deployed condition. On the other hand, distal translation of second end 584 of actuator member 582 along slot 22b' pulls linkage bar 588 proximally (since linkage bar 588 is coupled to actuator member 582 on an opposite side of pin 586 as compared to second end 584 of actuator member 582), thereby pulling monopolar assembly 200 proximally towards the retracted condition. In other words, distal actuation of first end 583 of actuator member 582 effects deployment of monopolar assembly 200, while distal actuation of second end 584 of actuator member 582 effects retraction of monopolar assembly 200. The use and operation of forceps 10' with deployment mechanism 580 is otherwise similar to that detailed above with respect to deployment mechanism 80 and forceps 10 (FIG. 1).

Turning to FIGS. 13A-15B, another embodiment of a deployment mechanism is shown designated as deployment mechanism 680. Deployment mechanism 680 is shown configured for use with a forceps 10", which is similar to and may include any or all of the features of forceps 10 (FIG. 1). Forceps 10" differs from forceps 10 (FIG. 1) in the configuration of housing 20" and the configuration of monopolar assembly 200". More specifically, housing 20" of forceps 10" includes a slot 22a" disposed on either (or both) side of housing 20" and an aperture 22b" defined through an upper portion of housing 20", although other positions of slot(s) 22a" and/or aperture 22b" are also contemplated. Monopolar assembly 200" is similar to monopolar assembly 200 (FIGS. 2-5) and generally includes an insulative sleeve 210", an energizable rod member 220", and a proximal hub 230". Monopolar assembly 200" differs from monopolar assembly 200 (FIGS. 2-5) in that proximal hub 230" of monopolar assembly 200" defines an elongated configuration including a plurality of ratchet teeth 232" extending longitudinally therealong.

Deployment mechanism 680 includes a plunger assembly 682, an actuator assembly 684, and a fixed gear 686. Fixed gear 686 is rotatably mounted within housing 20". More specifically, fixed gear 686 is disposed in meshed engagement with ratchet teeth 232" of proximal hub 230" of monopolar assembly 200". As such, rotation of fixed gear 686 in a counterclockwise direction (from the orientation shown in FIGS. 13B, 14B, and 15B) urges proximal hub 230" and, thus, monopolar assembly 200" distally towards the deployed condition, while rotation of fixed gear 686 in a clockwise direction (from the orientation shown in FIGS. 13B, 14B, and 15B) urges proximal hub 230" and, thus, monopolar assembly 200" proximally towards the storage condition.

Actuator assembly 684 includes a rotatable actuator 685a, a pin 685b, a first gear 685c, and a biasing member 685d. Pin 685b extends through slot 22a" defined within housing 20" and engages the externally-disposed rotatable actuator 685a with the internally-disposed first gear 685c. As such, rotation of rotatable actuator 685a effects corresponding rotation of first gear 685c. Pin 685b is slidable through slot 22a" and relative to housing 20". Further, biasing member 685d is coupled between pin 685b and housing 20" to bias pin 685b distally such that rotatable actuator 685a is biased towards the distal end of slot 22a" and such that first gear 685c is biased distally into meshed engagement with fixed gear 686. With first gear 685c engaged with fixed gear 686, rotatable actuator 685a may be actuated, e.g., rotated in a clockwise direction (from the orientation shown in FIGS. 13A, 14A, and 15A), to rotate fixed gear 686 in a counterclockwise direction to thereby deploy monopolar assembly 200".

Plunger assembly 682 includes a shaft 683a, a depressible actuator 683b, and a second gear 683c. Shaft 683a extends through aperture 22b" of housing 20" and includes depressible actuator 683b engaged at the externally-disposed end thereof and second gear 683c rotatably coupled at the internally-disposed end thereof. Depressible actuator 683b is configured to be manipulated between an extended position (FIGS. 13A-14B), wherein depressible actuator 683b is spaced-apart from housing 20", and a depressed position (FIGS. 15A and 15B), wherein depressible actuator 683b is positioned adjacent housing 20". Movement of depressible actuator 683b, in turn, moves second gear 683c into or out of engagement between first gear 685c and fixed gear 686. More specifically, with depressible actuator 683b disposed in the extended position, first gear 685c is directly engaged with fixed gear 686 such that rotatable actuator 685a may be actuated to deploy monopolar assembly 200". On the other hand, when depressible actuator 683b is moved to the depressed position, second gear 683c is urged into position between first gear 685c and fixed gear 686, e.g., via urging actuator assembly 684 proximally along slot 22a" against the bias of biasing member 685d. In this configuration, second gear 683c serves as a reverser such that subsequent actuation of rotatable actuator 685a in the same manner as above serves to rotate first gear 685c in a clockwise direction (from the orientation shown in FIGS. 13A, 14A, and 15A), second gear 683c in a counterclockwise direction, and fixed gear 686 in a clockwise direction, to thereby retract monopolar assembly 200".

Figure 13B:
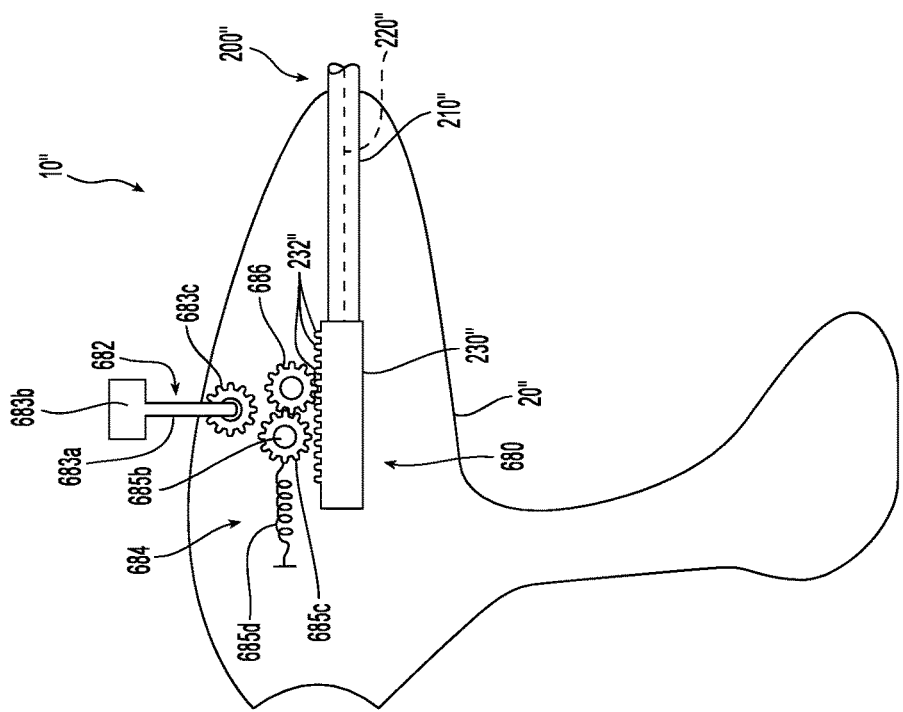
FIG. 13B is a side view of the proximal end of the forceps of FIG. 13A, with a portion of the housing and internal components thereof removed to unobstructively illustrate the proximal end of the monopolar assembly and the deployment mechanism for deploying the monopolar assembly, wherein the deployment mechanism is disposed in an un-actuated condition corresponding to the storage condition of the monopolar assembly.
Figure 13A:
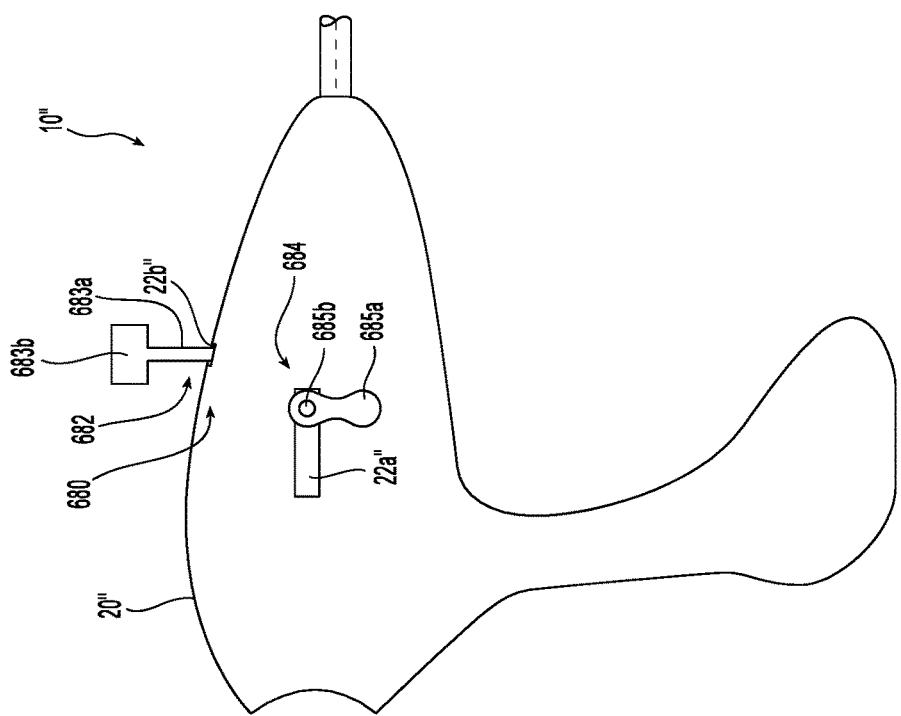
FIG. 13A is a side view of the proximal end of another forceps similar to the forceps of FIG. 1, wherein a deployment mechanism is disposed in an un-actuated condition corresponding to the storage condition of the monopolar assembly.

In use, initially, as shown in FIGS. 13A and 13B, depressible actuator 683b is disposed in the extended position and actuator assembly 684 is biased distally via biasing member 685d such that first gear 685c is engaged with fixed gear 686. In order to deploy monopolar assembly 200" from this position, rotatable actuator 685a is rotated in a clockwise direction sufficiently so as to urge proximal hub 230" distally to the deployed condition of monopolar assembly 200".

Figure 14B:
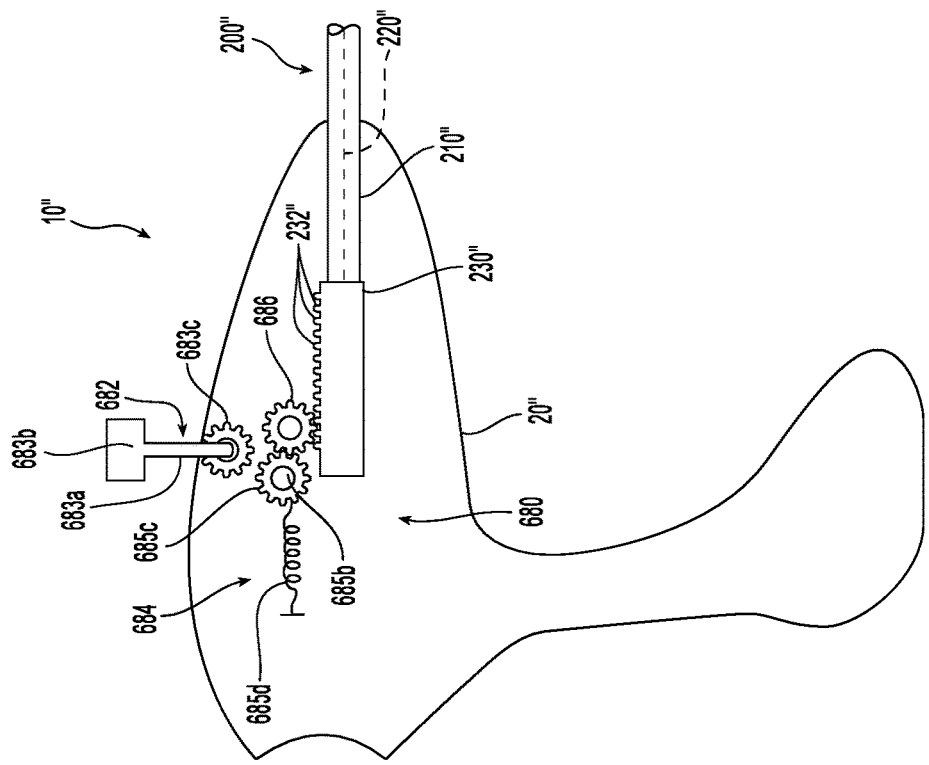
FIG. 14B is a side view of the proximal end of the forceps of FIG. 13A, with a portion of the housing and internal components thereof removed to unobstructively illustrate the proximal end of the monopolar assembly and the deployment mechanism for deploying the monopolar assembly, wherein the deployment mechanism is disposed in an actuated condition corresponding to the deployed condition of the monopolar assembly.
Figure 14A:
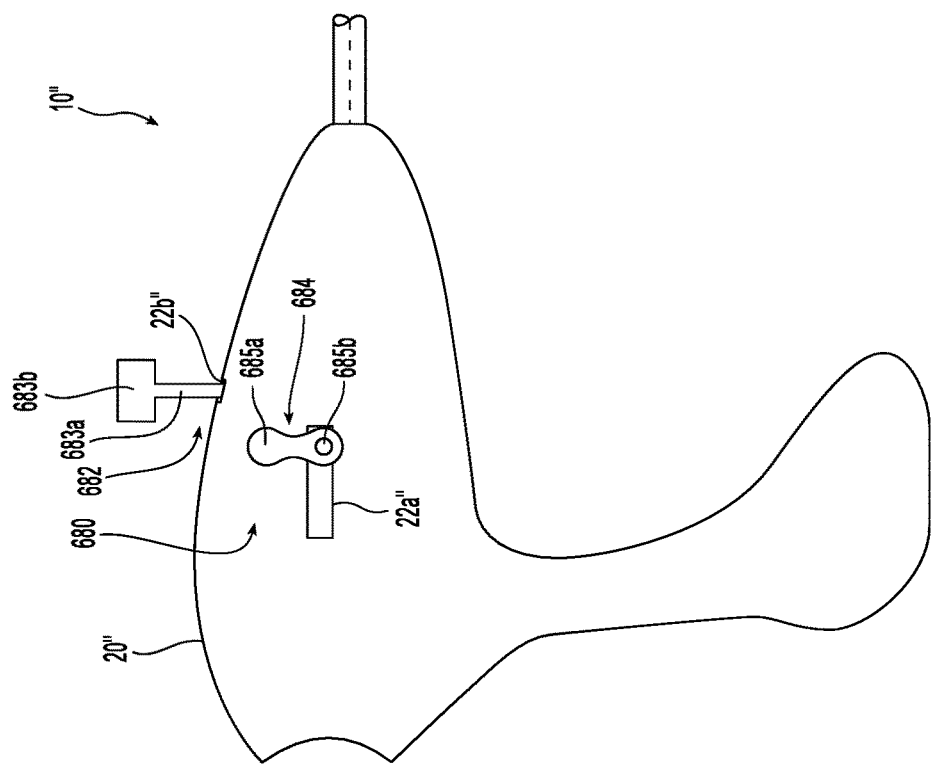
FIG. 14A is a side view of the proximal end of the forceps of FIG. 13A, wherein the deployment mechanism is disposed in an actuated condition corresponding to the deployed condition of the monopolar assembly.
Figure 15B:
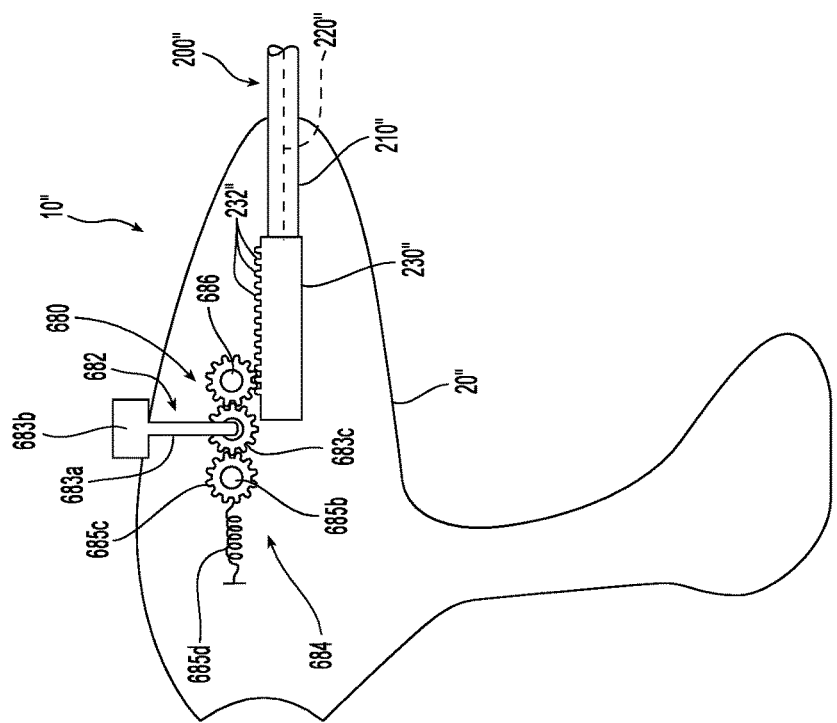
FIG. 15B is a side view of the proximal end of the forceps of FIG. 13A, with a portion of the housing and internal components thereof removed to unobstructively illustrate the proximal end of the monopolar assembly and the deployment mechanism for deploying the monopolar assembly, wherein the deployment mechanism is disposed in an actuated condition corresponding to the deployed condition of the monopolar assembly, with the reverser assembly engaged with the deployment mechanism.
Figure 15A:
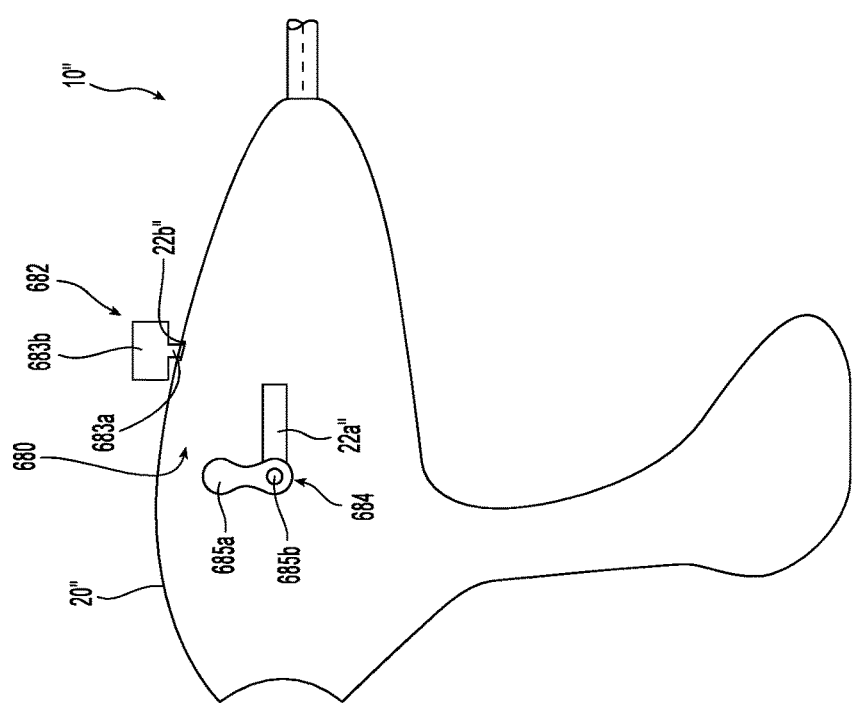
FIG. 15A is a side view of the proximal end of the forceps of FIG. 13A, wherein the deployment mechanism is disposed in an actuated condition corresponding to the deployed condition of the monopolar assembly, with a reverser assembly engaged with the deployment mechanism.

Deployment mechanism 680 is shown in FIGS. 14A and 14B corresponding to the deployed condition of monopolar assembly 200". In order to retract monopolar assembly 200" from this position, depressible actuator 683b is first moved to the depressed position, shown in FIGS. 15A and 15B, wherein second gear 683c is interdisposed between first gear 685c and fixed gear 686. Once depressible actuator 683b is disposed in the depressed position, sufficient actuation of rotatable actuator 685a in the same manner as the initial actuation may be effected to urge proximal hub 230" proximally to the storage condition of monopolar assembly 200". For re-deployment, depressible actuator 683b is moved back to the extended position (FIGS. 13A and 13B), and rotatable actuator 685a is re-actuated, similarly as above. The use and operation of forceps 10" with deployment mechanism 680 is otherwise similar to that detailed above with respect to deployment mechanism 80 and forceps 10 (FIG. 1). Other configurations utilizing a reversing gear are also contemplated such as those utilizing various fixed and moving gears and/or fixed and moving gear racks, and/or those utilizing translating and/or rotating input motions.

The various embodiments disclosed herein may also be configured to work with robotic surgical systems and what is commonly referred to as "Telesurgery." Such systems employ various robotic elements to assist the surgeon in the operating room and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various drawing figures, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
   a housing;
   an energizable member movable relative to the housing between a storage position and a deployed position; and
   a deployment mechanism coupled to the housing and the energizable member and configured to selectively move the energizable member between the storage position and the deployed position, the deployment mechanism including:
      a fixed gear operably coupled to the energizable member, wherein the fixed gear is rotatable in a first direction to move the energizable member towards the deployed position and in a second, opposite direction to move the energizable member towards the storage position;
      an actuator assembly including a first actuator and a first gear, the first actuator movable from an un-actuated position to an actuated position, the actuator assembly movable relative to the fixed gear between an engaged position, wherein the first gear is disposed in meshed engagement with the fixed gear, and a spaced-apart position, wherein the first gear is spaced-apart from the fixed gear; and
      a reversing assembly coupled to the housing and including a second actuator and a second gear, the second actuator movable between a removed position, wherein the first gear is disposed in the engaged position and the second gear is disengaged from the first gear and the fixed gear, and an inserted position, wherein the first gear is moved to the spaced-apart position and the second gear is engaged between the first gear and the fixed gear.

2. The surgical instrument according to claim 1, wherein movement of the first actuator from the un-actuated position to the actuated position moves the energizable member from the storage position to the deployed position when the second actuator is disposed in the removed position, and wherein movement of the first actuator from the un-actuated position to the actuated position moves the energizable member from the deployed position to the storage position when the second actuator is disposed in the inserted position.

3. The surgical instrument according to claim 1, wherein the first actuator is biased towards the engaged position.

4. The surgical instrument according to claim 1, wherein the first actuator is slidable along a slot defined within the housing between the engaged position and the spaced-apart position.

5. The surgical instrument according to claim 1, wherein the first actuator is rotatable relative to the housing between the un-actuated position and the actuated position and wherein the second actuator is translatable relative to the housing between the removed position and the inserted position.

6. A surgical instrument, comprising:
   a housing;
   a shaft extending distally from the housing;
   an end effector assembly disposed at a distal end of the shaft;
   a deployable assembly including an energizable member and an insulative member, the deployable assembly movable relative to the end effector assembly between a storage position and a deployed position; and
   a deployment mechanism coupled to the housing and the deployable assembly and configured to selectively move the deployable assembly between the storage position and the deployed position, the deployment mechanism including:
      a fixed gear operably coupled to the deployable assembly, wherein the fixed gear is rotatable in a first direction to move the deployable assembly towards the deployed position and in a second, opposite direction to move the deployable assembly towards the storage position;
      an actuator assembly including a first actuator and a first gear, the first actuator movable from an un-actuated position to an actuated position, the actuator assembly movable relative to the fixed gear between an engaged position, wherein the first gear is disposed in meshed engagement with the fixed gear, and a spaced-apart position, wherein the first gear is spaced-apart from the fixed gear; and
      a reversing assembly coupled to the housing and including a second actuator and a second gear, the second actuator movable between a removed position, wherein the first gear is disposed in the engaged position and the second gear is disengaged from the first gear and the fixed gear, and an inserted position, wherein the first gear is moved to the spaced-apart position and the second gear is engaged between the first gear and the fixed gear.

7. The surgical instrument according to claim 6, wherein movement of the first actuator from the un-actuated position to the actuated position moves the deployable assembly from the storage position to the deployed position when the second actuator is disposed in the removed position, and wherein movement of the first actuator from the un-actuated position to the actuated position moves the deployable assembly from the deployed position to the storage position when the second actuator is disposed in the inserted position.

8. The surgical instrument according to claim 6, wherein the first actuator is biased towards the engaged position.

9. The surgical instrument according to claim 6, wherein the first actuator is slidable along a slot defined within the housing between the engaged position and the spaced-apart position.

10. The surgical instrument according to claim 6, wherein the first actuator is rotatable relative to the housing between the un-actuated position and the actuated position and wherein the second actuator is translatable relative to the housing between the removed position and the inserted position.

11. The surgical instrument according to claim 6, wherein the end effector assembly includes first and second jaw members configured to treat tissue in a bipolar mode of operation.

12. The surgical instrument according to claim 11, wherein, in the deployed position, the insulative member is disposed about the jaw members and the energizable member extends distally from the jaw members for treating tissue in a monopolar mode of operation.

* * * * *